United States Patent
Blomquist et al.

(10) Patent No.: US 8,718,949 B2
(45) Date of Patent: May 6, 2014

(54) INSULIN PUMP WITH BLOOD GLUCOSE MODULES

(75) Inventors: Michael Blomquist, Blaine, MN (US);
Kevin Kopp, St. Paul, MN (US);
Thomas Alan Savard, Arden Hills, MN (US)

(73) Assignee: Tandem Diabetes Care, Inc., San Diego, CA (US)

( * ) Notice: Subject to any disclaimer, the term of this patent is extended or adjusted under 35 U.S.C. 154(b) by 0 days.

(21) Appl. No.: 13/481,302

(22) Filed: May 25, 2012

(65) Prior Publication Data

US 2012/0238854 A1 Sep. 20, 2012

Related U.S. Application Data

(60) Continuation of application No. 12/908,218, filed on Oct. 20, 2010, which is a division of application No. 11/970,232, filed on Jan. 7, 2008, now abandoned.

(51) Int. Cl.
*G01N 33/48* (2006.01)
*A61B 5/145* (2006.01)
*A61M 5/142* (2006.01)

(52) U.S. Cl.
CPC ...... *A61B 5/14532* (2013.01); *A61M 2230/201* (2013.01); *A61M 5/14244* (2013.01)
USPC .............................. 702/19; 600/365; 604/67

(58) Field of Classification Search
CPC .................. A61B 5/14532; A61M 2230/201; A61M 5/14244
USPC .......... 600/365; 604/65–67, 131–155; 702/19
See application file for complete search history.

(56) References Cited

U.S. PATENT DOCUMENTS

| | | |
|---|---|---|
| 4,475,901 A | 10/1984 | Kraegen et al. |
| 5,153,827 A | 10/1992 | Coutre et al. |
| 5,181,910 A | 1/1993 | Scanlon |
| 5,338,157 A | 8/1994 | Blomquist |
| 5,364,346 A | 11/1994 | Schrezenmeir |
| 5,368,562 A | 11/1994 | Blomquist et al. |
| 5,389,078 A | 2/1995 | Zalesky et al. |
| 5,485,408 A | 1/1996 | Blomquist |
| 5,558,638 A | 9/1996 | Evers et al. |

(Continued)

FOREIGN PATENT DOCUMENTS

| | | |
|---|---|---|
| DE | 10352456 | 7/2005 |
| WO | WO0045696 | 8/2000 |

(Continued)

OTHER PUBLICATIONS

Walsh et al., "Select and Test Your Basal Rates", Pumping Insulin Fourth Edition, Chapter 11 (2006) 29 pages.

(Continued)

*Primary Examiner* — Nicholas Lucchesi
*Assistant Examiner* — Gerald Landry, II
(74) *Attorney, Agent, or Firm* — Patterson Thuente Pedersen, P.A.

(57) ABSTRACT

An apparatus comprising a pump, an input configured to receive information related to a user, a user interface, and a controller communicatively coupled to the pump, the input, and the user interface. The controller includes a timing module configured to initiate delivery of a drug in time and to adjust delivery according to the received information. Other devices, systems, and methods are disclosed.

9 Claims, 10 Drawing Sheets

(56) References Cited

U.S. PATENT DOCUMENTS

| | | |
|---|---|---|
| 5,658,250 A | 8/1997 | Blomquist et al. |
| 5,658,252 A | 8/1997 | Johnson |
| 5,665,065 A | 9/1997 | Colman et al. |
| 5,669,877 A | 9/1997 | Blomquist |
| 5,695,473 A | 12/1997 | Olsen |
| 5,810,771 A | 9/1998 | Blomquist |
| 5,876,370 A | 3/1999 | Blomquist |
| 5,879,143 A | 3/1999 | Cote et al. |
| 5,935,099 A | 8/1999 | Peterson et al. |
| 5,935,106 A | 8/1999 | Olsen |
| 6,024,539 A | 2/2000 | Blomquist |
| 6,077,055 A | 6/2000 | Vilks |
| 6,241,704 B1 | 6/2001 | Peterson et al. |
| 6,248,057 B1 | 6/2001 | Mavity et al. |
| 6,249,717 B1 | 6/2001 | Nicholson et al. |
| 6,422,057 B1 | 7/2002 | Anderson |
| 6,475,180 B2 | 11/2002 | Peterson et al. |
| 6,544,212 B2 | 4/2003 | Galley et al. |
| 6,551,276 B1 | 4/2003 | Mann et al. |
| 6,554,798 B1 | 4/2003 | Mann et al. |
| 6,558,320 B1 | 5/2003 | Causey, III et al. |
| 6,558,351 B1 | 5/2003 | Steil et al. |
| 6,623,698 B2 | 9/2003 | Kuo |
| 6,641,533 B2 | 11/2003 | Causey, III et al. |
| 6,650,951 B1 | 11/2003 | Jones et al. |
| 6,656,114 B1 | 12/2003 | Poulsen et al. |
| 6,744,350 B2 | 6/2004 | Blomquist |
| 6,809,653 B1 | 10/2004 | Mann et al. |
| 6,852,104 B2 | 2/2005 | Blomquist |
| 6,872,200 B2 | 3/2005 | Mann et al. |
| 6,895,263 B2 | 5/2005 | Shin et al. |
| 6,936,029 B2 | 8/2005 | Mann et al. |
| 6,970,742 B2 | 11/2005 | Mann et al. |
| 6,979,326 B2 | 12/2005 | Mann et al. |
| 6,997,920 B2 | 2/2006 | Mann et al. |
| 6,999,854 B2 | 2/2006 | Roth |
| 7,004,928 B2 | 2/2006 | Aceti et al. |
| 7,025,743 B2 | 4/2006 | Mann et al. |
| 7,033,338 B2 | 4/2006 | Vilks et al. |
| 7,041,082 B2 | 5/2006 | Blomquist et al. |
| 7,098,803 B2 | 8/2006 | Mann et al. |
| 7,109,878 B2 | 9/2006 | Mann et al. |
| 7,181,505 B2 | 2/2007 | Haller et al. |
| 7,282,029 B1 | 10/2007 | Poulsen et al. |
| 7,324,012 B2 | 1/2008 | Mann et al. |
| 7,483,743 B2 | 1/2009 | Mann et al. |
| 7,515,060 B2 | 4/2009 | Blomquist |
| 7,647,237 B2 | 1/2010 | Malave et al. |
| 7,704,226 B2 | 4/2010 | Mueller et al. |
| 7,715,893 B2 | 5/2010 | Kamath et al. |
| 7,734,323 B2 | 6/2010 | Blomquist et al. |
| 7,768,408 B2 | 8/2010 | Reggiardo et al. |
| 7,819,843 B2 | 10/2010 | Mann et al. |
| 7,875,022 B2 | 1/2011 | Wenger et al. |
| 7,884,729 B2 | 2/2011 | Reggiardo et al. |
| 7,890,295 B2 | 2/2011 | Shin et al. |
| 7,935,076 B2 | 5/2011 | Estes et al. |
| 7,967,773 B2 | 6/2011 | Amborn et al. |
| 7,981,034 B2 | 7/2011 | Jennewine et al. |
| 8,192,394 B2 | 6/2012 | Estes et al. |
| 8,202,267 B2 | 6/2012 | Field et al. |
| 8,234,126 B1 | 7/2012 | Estes |
| 8,234,128 B2 | 7/2012 | Martucci et al. |
| 8,250,483 B2 | 8/2012 | Blomquist |
| 8,251,904 B2 | 8/2012 | Zivitz et al. |
| 8,262,617 B2 | 9/2012 | Aeschlimann et al. |
| 8,287,514 B2 | 10/2012 | Miller et al. |
| 8,328,754 B2 | 12/2012 | Estes et al. |
| 8,346,399 B2 | 1/2013 | Blomquist |
| 8,372,040 B2 | 2/2013 | Huang et al. |
| 8,414,523 B2 | 4/2013 | Blomquist et al. |
| 8,451,230 B2 | 5/2013 | Celentano et al. |
| 8,552,880 B2 | 10/2013 | Kopp et al. |
| 2001/0001144 A1 | 5/2001 | Kapp |
| 2001/0031944 A1 | 10/2001 | Peterson et al. |
| 2002/0002326 A1 | 1/2002 | Causey et al. |
| 2002/0065454 A1 | 5/2002 | Lebel et al. |
| 2002/0107476 A1 | 8/2002 | Mann et al. |
| 2002/0183693 A1 | 12/2002 | Peterson et al. |
| 2003/0036683 A1 | 2/2003 | Kehr et al. |
| 2003/0065308 A1 | 4/2003 | Lebel et al. |
| 2003/0114836 A1 | 6/2003 | Estes et al. |
| 2003/0163088 A1 | 8/2003 | Blomquist |
| 2003/0163223 A1 | 8/2003 | Blomquist |
| 2003/0163789 A1 | 8/2003 | Blomquist |
| 2003/0212364 A1 | 11/2003 | Mann et al. |
| 2004/0015102 A1 | 1/2004 | Cummings et al. |
| 2004/0015132 A1 | 1/2004 | Brown |
| 2004/0068230 A1 | 4/2004 | Estes et al. |
| 2004/0073095 A1 | 4/2004 | Causey, III et al. |
| 2004/0254434 A1 | 12/2004 | Goodnow et al. |
| 2005/0022274 A1 | 1/2005 | Campbell |
| 2005/0030164 A1 | 2/2005 | Blomquist |
| 2005/0137530 A1 | 6/2005 | Campbell et al. |
| 2005/0143864 A1 | 6/2005 | Blomquist |
| 2005/0171513 A1 | 8/2005 | Mann et al. |
| 2005/0197621 A1* | 9/2005 | Poulsen et al. ............... 604/67 |
| 2005/0203349 A1* | 9/2005 | Nanikashvili ................ 600/300 |
| 2005/0203360 A1* | 9/2005 | Brauker et al. ............... 600/345 |
| 2006/0001550 A1 | 1/2006 | Mann et al. |
| 2006/0094985 A1* | 5/2006 | Aceti et al. ................... 600/575 |
| 2006/0132292 A1 | 6/2006 | Blomquist |
| 2006/0173444 A1* | 8/2006 | Choy et al. ................. 604/891.1 |
| 2006/0202859 A1 | 9/2006 | Mastrototaro et al. |
| 2006/0224109 A1 | 10/2006 | Steil et al. |
| 2006/0264895 A1 | 11/2006 | Flanders |
| 2006/0271020 A1 | 11/2006 | Huang et al. |
| 2007/0016127 A1 | 1/2007 | Staib et al. |
| 2007/0106135 A1 | 5/2007 | Sloan et al. |
| 2007/0118405 A1 | 5/2007 | Campbell et al. |
| 2007/0156033 A1 | 7/2007 | Causey, III et al. |
| 2007/0255250 A1 | 11/2007 | Moberg et al. |
| 2007/0299389 A1 | 12/2007 | Halbert et al. |
| 2008/0004601 A1 | 1/2008 | Jennewine et al. |
| 2008/0030369 A1 | 2/2008 | Mann et al. |
| 2008/0033357 A1 | 2/2008 | Mann et al. |
| 2008/0033361 A1 | 2/2008 | Evans et al. |
| 2008/0065007 A1 | 3/2008 | Peterson |
| 2008/0065016 A1 | 3/2008 | Peterson |
| 2008/0132844 A1 | 6/2008 | Peterson |
| 2008/0154513 A1* | 6/2008 | Kovatchev et al. ............ 702/19 |
| 2008/0172026 A1 | 7/2008 | Blomquist |
| 2008/0172027 A1 | 7/2008 | Blomquist |
| 2008/0172028 A1 | 7/2008 | Blomquist |
| 2008/0172029 A1 | 7/2008 | Blomquist |
| 2008/0172030 A1 | 7/2008 | Blomquist |
| 2008/0172031 A1 | 7/2008 | Blomquist |
| 2008/0206799 A1 | 8/2008 | Blomquist |
| 2008/0228056 A1 | 9/2008 | Blomquist et al. |
| 2008/0249470 A1 | 10/2008 | Malave et al. |
| 2008/0255517 A1 | 10/2008 | Nair et al. |
| 2008/0300572 A1 | 12/2008 | Rankers |
| 2009/0069749 A1 | 3/2009 | Miller et al. |
| 2009/0069787 A1 | 3/2009 | Estes et al. |
| 2009/0156990 A1 | 6/2009 | Wenger et al. |
| 2009/0163855 A1 | 6/2009 | Shin et al. |
| 2009/0177142 A1 | 7/2009 | Blomquist et al. |
| 2009/0177147 A1 | 7/2009 | Blomquist et al. |
| 2009/0177154 A1 | 7/2009 | Blomquist |
| 2009/0177180 A1 | 7/2009 | Rubalcaba |
| 2009/0254037 A1 | 10/2009 | Bryant, Jr. et al. |
| 2009/0267774 A1 | 10/2009 | Enegren et al. |
| 2009/0267775 A1 | 10/2009 | Enegren et al. |
| 2009/0270705 A1 | 10/2009 | Enegren et al. |
| 2010/0010330 A1 | 1/2010 | Rankers et al. |
| 2010/0030387 A1 | 2/2010 | Sen |
| 2010/0056993 A1 | 3/2010 | Chase |
| 2010/0160740 A1 | 6/2010 | Cohen et al. |
| 2010/0161236 A1 | 6/2010 | Cohen et al. |
| 2010/0161346 A1 | 6/2010 | Getschmann et al. |
| 2010/0162786 A1 | 7/2010 | Keenan et al. |
| 2010/0174553 A1 | 7/2010 | Kaufman et al. |
| 2010/0185142 A1 | 7/2010 | Kamen et al. |
| 2010/0185175 A1 | 7/2010 | Kamen et al. |

(56) References Cited

U.S. PATENT DOCUMENTS

| | | |
|---|---|---|
| 2010/0286653 A1 | 11/2010 | Kubel et al. |
| 2010/0292634 A1* | 11/2010 | Kircher et al. ............... 604/66 |
| 2010/0312085 A1 | 12/2010 | Andrews et al. |
| 2010/0324398 A1* | 12/2010 | Tzyy-Ping ............... 600/365 |
| 2011/0033833 A1 | 2/2011 | Blomquist et al. |
| 2011/0040247 A1 | 2/2011 | Mandro et al. |
| 2011/0040251 A1 | 2/2011 | Blomquist et al. |
| 2011/0047499 A1 | 2/2011 | Mandro et al. |
| 2011/0058485 A1 | 3/2011 | Sloan |
| 2011/0060281 A1 | 3/2011 | Aeschlimann et al. |
| 2011/0082439 A1 | 4/2011 | Wenger et al. |
| 2011/0087165 A1 | 4/2011 | Amborn et al. |
| 2011/0124999 A1 | 5/2011 | Reggiardo et al. |
| 2011/0126188 A1 | 5/2011 | Bernstein et al. |
| 2011/0160654 A1 | 6/2011 | Hanson et al. |
| 2011/0178461 A1 | 7/2011 | Chong et al. |
| 2011/0178717 A1 | 7/2011 | Goodnow et al. |
| 2011/0205065 A1 | 8/2011 | Strachan et al. |
| 2011/0213306 A1 | 9/2011 | Hanson et al. |
| 2012/0029941 A1 | 2/2012 | Malave et al. |
| 2012/0232520 A1 | 9/2012 | Sloan et al. |

FOREIGN PATENT DOCUMENTS

| | | |
|---|---|---|
| WO | WO0074753 | 12/2000 |
| WO | WO0152727 | 7/2001 |
| WO | WO2006061169 | 6/2006 |
| WO | WO2007149533 | 12/2007 |
| WO | WO 2007149533 A2 * | 12/2007 |
| WO | WO2008048582 | 4/2008 |
| WO | WO2008112078 | 8/2008 |
| WO | WO2009035759 | 3/2009 |
| WO | WO2009088983 | 7/2009 |
| WO | WO2009089028 | 7/2009 |
| WO | WO2011068648 | 6/2011 |

OTHER PUBLICATIONS

International Search Report and Written Opinion for International Application No. PCT/US2008/002536 mailed Sep. 4, 2008.

International Search Report and Written Opinion for International Application No. PCT/US200900034 dated May 27, 2009.

"The Use of Insulin Pumps with Meal Bolus Alarms in Children with Type 1 Diabetes to Improve Glycemic Control", Diabetes Care, vol. 29, No. 5. May 2006. pp. 1012-1015.

Walsh, "Diabetes Technology Concept 1: Super Bolus" Online.http://www.diabetesnet.com/diabetes_technology/super_bolus.php> Sep. 17, 2007. (3 pages).

Walsh et al., "Pumping Insulin: Everything you need to for success on a Smart Insulin Pump", Torrey Pines Press, Sandiego . 2006.

International Preliminary Report and Written Opinion for International Application No. PCT/US2010/056233 dated Jun. 5, 2012.

PCT Search Report dated Aug. 31, 2011 for PCT Application No. PCT/US2010/056233 filed Nov. 10, 2010.

International Search Report and Written Opinion for International Application No. PCT/US2007/024423 dated May 19, 2008.

International Search Report and Written Opinion for International Application No. PCT/US2009/000106 dated May 13, 2009.

Application and File History for U.S. Appl. No. 11/685,617, filed Mar. 13, 2007, inventors Blomquist et al.

Application and File History for U.S. Appl. No. 11/970,232, filed Jan. 7, 2008, inventors Blomquist et al.

Application and File History for U.S. Appl. No. 12/908,218, filed Oct. 20, 2010, inventors Blomquist et al.

Application and File History for U.S. Appl. No. 12/631,077, filed Dec. 4, 2009, inventors Kopp et al.

Application and File History for U.S. Appl. No. 11/679,712, filed Feb. 27, 2007, inventor Blomquist.

Application and File History for U.S. Appl. No. 11/970,691, filed Jan. 8, 2008 inventor Blomquist.

* cited by examiner

INSULIN PUMP WITH BLOOD GLUCOSE MODULES

RELATED APPLICATION

This application is a continuation of application Ser. No. 12/908,218 filed Oct. 20, 2010, which in turn is a division of application Ser. No. 11/970,232 filed Jan. 7, 2008, which is hereby fully incorporated herein by reference.

BACKGROUND OF THE INVENTION

People who suffer from diabetes require insulin to keep their blood glucose level as close as possible to normal levels. It is essential for people with diabetes to manage their blood glucose level to within a normal range. Complications from diabetes can include heart disease (cardiovascular disease), blindness (retinopathy), nerve damage (neuropathy), and kidney damage (nephropathy). Insulin is a hormone that reduces the level of blood glucose in the body. Normally, insulin is produced by beta cells in the pancreas. In non-diabetic people, the beta cells release insulin to satisfy two types of insulin needs. The first type is a low-level of background insulin that is released throughout the day. The second type is a quick release of a higher-level of insulin in response to eating. Insulin therapy replaces or supplements insulin produced by the pancreas.

Conventional insulin therapy typically involves one or two injections a day. The low number of injections has the disadvantage of allowing larger variations in a person's insulin levels. Some people with diabetes manage their blood glucose level with multiple daily injections (MDI). MDI may involve more than three injections a day and four or more blood glucose tests a day. MDI offers better control than conventional therapy. However, insulin injections are inconvenient and require a diabetic person to track the insulin doses, the amount of carbohydrates eaten, and their blood glucose levels among other information critical to control.

It is important for a diabetic person to be treated with the proper amount of insulin. As discussed previously, high blood sugar can lead to serious complications. Conversely, a person with low blood sugar can develop hypoglycemia. Ideally, insulin therapy mimics the way the body works. An insulin pump is one way to mimic the body's insulin production. An insulin pump can provide a background or basal infusion of insulin throughout the day and provide a quick release or bolus of insulin when carbohydrates are eaten. If a person develops high blood sugar, a correction bolus of insulin can be delivered by the pump to correct it. While insulin pumps improve convenience and flexibility for a diabetic person, they can be sophisticated devices. Some insulin pumps can be difficult to program. Proper use of an insulin pump requires a user to go through a learning curve to properly treat their diabetes using the insulin pump.

SUMMARY

In an embodiment, an apparatus comprises a pump configured to deliver a drug from a cartridge; a user interface; a memory to store guideline parameters related to use of the apparatus; and a controller communicatively coupled to the pump, the memory, and the user interface, wherein the controller includes: a comparison module configured to compare patient use parameters to the stored guideline parameters; and a scoring module configured to calculate a score indicative of efficacy of patient pump use based on a comparison by the comparison module, and wherein the controller is configured to communicate advice to the user on how to increase the efficacy of patient pump use.

In an embodiment, a method comprises monitoring patient use of a device that includes a pump, wherein the monitoring includes comparing patient use parameters to stored guideline parameters; calculating a score indicative of efficacy of patient pump use based on the monitoring; and communicating advice to the user on how to increase pump efficacy.

In an embodiment, an apparatus comprises a pump configured to deliver a drug therapy; a memory configured to store a delivery pattern of the drug therapy; a user interface configured to receive time change information; and a controller communicatively coupled to the pump, the memory, and the user interface, wherein the controller includes a timing module configured to shift the delivery pattern in time according to the received time change information.

In an embodiment, a method comprises receiving time change information into a device having a pump; and shifting a delivery pattern of the device in time according to the information received into the device.

This overview is intended present some subject matter of the patent application. It is not intended to provide an exclusive or exhaustive explanation of the invention. The detailed description is included to provide further information about the subject matter of the present patent application.

DETAILED DESCRIPTION OF THE DRAWINGS

Insulin Pumps can be sophisticated devices. Insulin pumps that help coach a person in the use of the device may cause the device to be more effective in treating a person's diabetes.

Figure 1A:
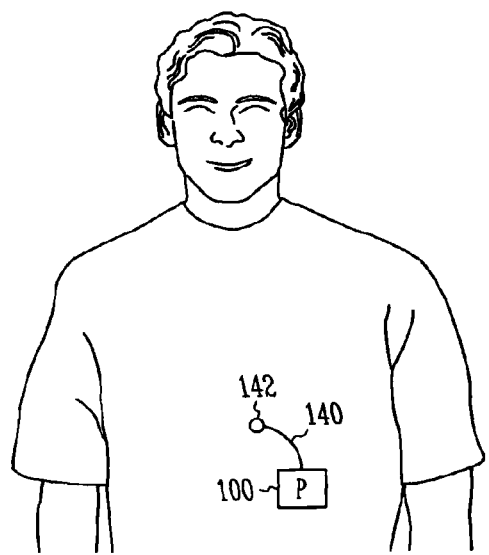
FIGS. 1A and 1B illustrate portions of a device that includes an insulin pump.
Figure 1B:
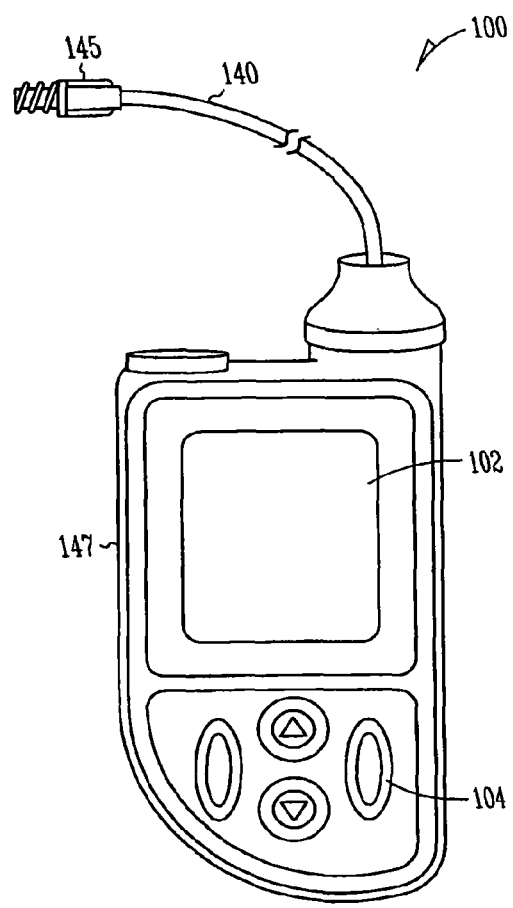

FIGS. 1A and 1B illustrate portions of a device 100 that includes an insulin pump. The device 100 includes a cassette or cartridge of insulin. The cartridge is connectable to infusion tubing 140 connectable to a patient such as by a Luer lock 145 or infusion set 142. The device 100 includes a display 102 and a user interface that may include the display 102 and include one or more keys 104. Because proper use of an insulin pump requires a user to go through a learning curve to properly treat their diabetes using the pump, it is desirable for a pump to provide assistance to the user, whether the user is a diabetic patient, a caregiver, or a clinician.

Adjusting Insulin According to Meals

It is important for a diabetic to properly control their blood glucose level. A meal bolus is an amount of insulin delivered in anticipation of, or in response to, eating a meal. Typically, the meal bolus insulin is to counteract or cover the amount the amount of carbohydrates in the meal. The proper amount of insulin can be influenced by many factors such as the nutrient content of the food in the meal. Nutrient content refers to the amount of carbohydrates, protein, and fat in the meal. Determining an appropriate amount of insulin in the meal bolus can be difficult for a pump user and may involve trial and error in finding the right meal bolus for certain meals.

Figure 2:
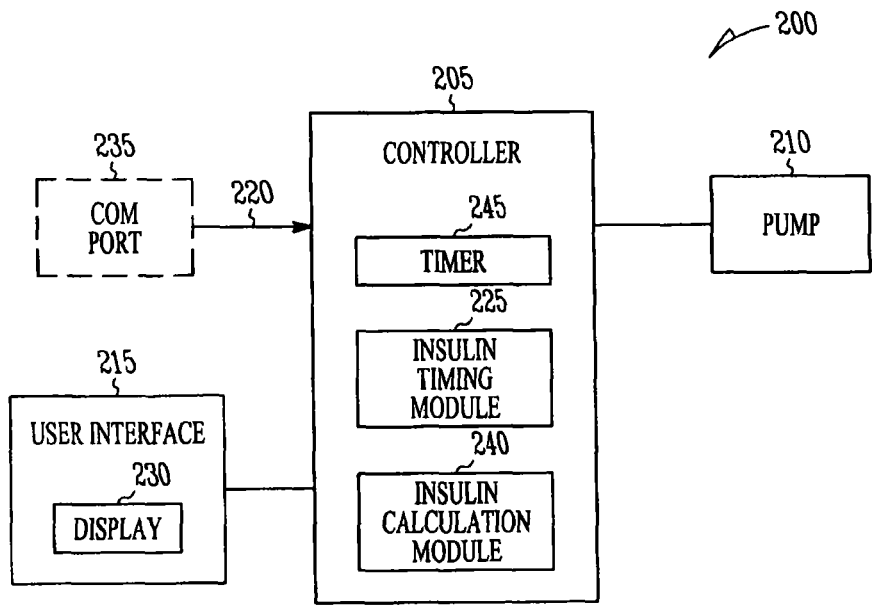
FIG. 2 is a block diagram of portions of an embodiment of a device to adjust delivery of meal-related insulin.

FIG. 2 is a block diagram of portions of an embodiment of a device 200 to automatically adjust meal-related insulin delivered with an insulin pump. The device 200 includes a controller 205. The controller 205 can be implemented using hardware circuits, firmware, software or any combination of hardware, firmware, and software. Examples, include a microcontroller, a logical state machine, and a processor such as a microprocessor, application specific integrated circuit (ASIC), or other type of processor. The controller 205 is configured to perform or execute a function or functions. Such functions correspond to modules, which are software, hardware, firmware or any combination thereof. Multiple functions may be performed in one or more modules. In some examples, software or firmware is provided on a computer readable medium. The computer readable medium includes instructions therein, which when processed (such as by the controller 205 for example) results in a device performing the functions described herein. Examples of a computer readable medium include a compact disc (CD), memory stick, or remote storage accessible via a communication network such as the internet or a cell phone network.

The device 200 also includes a pump 210 or pump mechanism to deliver insulin to a subject such as a patient or user. The pump 210 may be a positive displacement pump. Descriptions of an example of a medication pump to deliver insulin are found in Vilks et al., "Cartridge and Rod for Axially Loading a Medication Pump," U.S. Pat. No. 7,033,338, filed Feb. 28, 2002, which is incorporated herein by reference in its entirety. The device 200 also includes a user interface 215 and an input 220 that, together with the pump 210, are communicatively coupled to the controller 205. The communicative coupling allows the controller 205 to exchange electrical signals with the user interface 215, input 220, and pump 210 even though intervening circuitry may be present. The input 220 receives information into the device 200 related to managing diabetes of a user. This information may include physiologic data of the patient and/or any indications for the patient, such as any physical indications and indications of a drug therapy the patient is using. The information also may pertain to the meal the patient has eaten or plans to eat.

The controller 205 includes an insulin timing module 225 configured to initiate delivery of insulin in a time relation to when a meal is to be consumed by the user and to adjust delivery of the insulin according to the received information. The controller 205 may include a timer 245. After a timed duration after delivery of the insulin timed by the timer 245 or the insulin timing module 225, the controller generates a reminder to the user to eat. The reminder may be a visual alert displayed on a display 230 included in the user interface 215, or the device 200 may include a transducer or speaker and the generated reminder is an audible alert. In another example, the device may include a mechanical vibration mechanism and the generated reminder is a vibratory alert.

Figure 3:
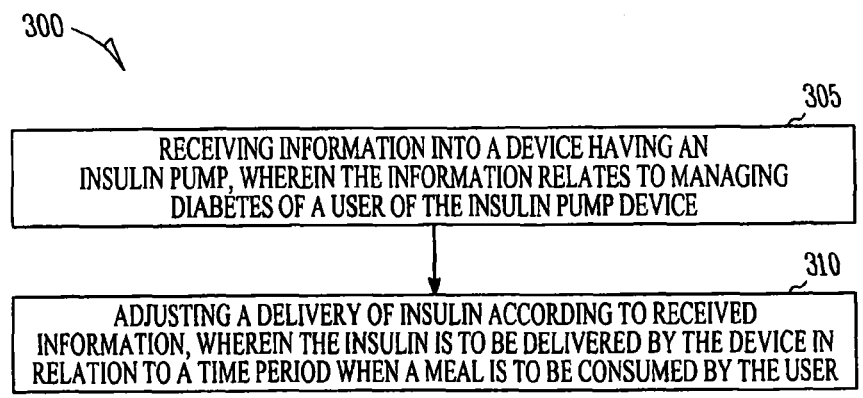
FIG. 3 is a flow diagram of an embodiment of a method to provide adjustment to a meal bolus for a pump user.

FIG. 3 is a flow diagram of an embodiment of a method 300 to automatically provide adjustment to a meal bolus for a pump user. At block 305, information is received into a device having an insulin pump. The received information relates to managing diabetes of a user of the insulin pump device. At block 310, delivery of insulin is adjusted according to the received information. The insulin is to be delivered by the device in relation to a time period when a meal is to be consumed by the user. The insulin may be delivered as a meal bolus prior to the meal, during the time the meal is scheduled, or after the meal. The insulin may be delivered as a change in a basal insulin rate pattern or profile.

Returning to FIG. 2, in some embodiments, the information related to managing diabetes of a user includes a blood glucose level of the user. In some embodiments, the device 200 includes a communication port 235 communicatively coupled to the input 220. The controller 205 is configured to receive information about the blood glucose level of the user via the communication port 235 from a separate second device. In some embodiments, the second device is a blood glucose monitor. In some embodiments, the communication port is a wireless port, such as an infrared (IR) port or a radio frequency (RF) port for example. In some embodiments, the communication port is a wired port, such as a serial port for example. In some embodiments, the controller 205 receives blood glucose information via the user interface 215, such as when the information is entered using a keypad included in the user interface.

Figure 4:
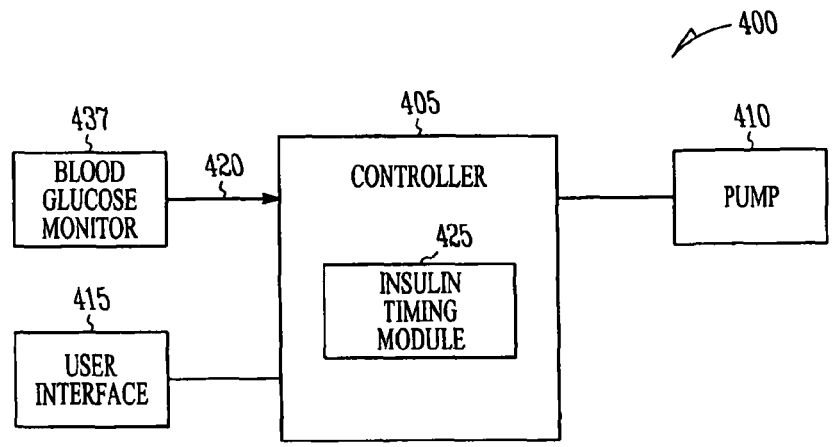
FIG. 4 shows another embodiment of a device to adjust meal-related insulin delivered with an insulin pump.

FIG. 4 shows another embodiment of a device 400 to automatically adjust meal-related insulin delivered with an insulin pump. The device 400 includes a pump to deliver insulin 410, a user interface 415, and an input 420, communicatively coupled to a controller 405 that includes an insulin timing module 425. The device 400 also includes a blood glucose monitor 437 communicatively coupled to the input 420. The blood glucose monitor 437 may be a continuous blood glucose monitor that includes a blood glucose sensor circuit to produce an electrical blood glucose signal representative of a blood glucose level of the patient. The blood glucose sensor circuit may sense blood glucose concentration from blood or from interstitial fluid. The blood glucose sensor circuit may include a sensor interface circuit to sample the blood glucose signal and may provide additional signal processing, such as filtering or amplification for example. The sensor interface circuit may provide sampled blood glucose data to the input 420. A description of a blood glucose sensor circuit can be found in Steil et al., "Closed Loop System for Controlling Insulin Infusion," U.S. Pat. No. 6,558,351, filed Jun. 1, 2000, which is incorporated herein by reference in its entirety.

It is desirable for diabetics to manage their blood glucose level to within a normal range. Returning to FIG. 2, the user may have a meal time scheduled or programmed into the device 200, and the controller 205 may initiate delivery of insulin in relation to a scheduled meal time. If the blood glucose information indicates that the blood glucose level of the user is low (e.g., the blood glucose level is lower than a threshold blood glucose level), the insulin timing module 225 may delay delivery of a meal bolus of insulin. In some embodiments, the user interface 215 includes a display 230. If the blood glucose information indicates that the blood glucose level of the user is high (e.g., the blood glucose level is higher than a threshold blood glucose level), the insulin timing module may display a recommendation that the user not eat. In some embodiments, if the blood glucose information indicates that the blood glucose level of the user is high, the insulin timing module may display a recommendation that the user initiate a correction bolus of insulin.

According to some embodiments, the information related to managing diabetes received by the controller 205 includes an indication whether the user has abnormal gastric emptying. An example of abnormal gastric emptying is gastroparesis. Gastroparesis refers to a digestive disorder in which the user has delayed emptying of food from the stomach into the lower intestine. The indication of abnormal gastric emptying may be stored in a memory communicatively coupled to the controller 205. The insulin timing module 225 may delay delivery of meal bolus when abnormal gastric emptying is indicated for the user.

Figure 5:
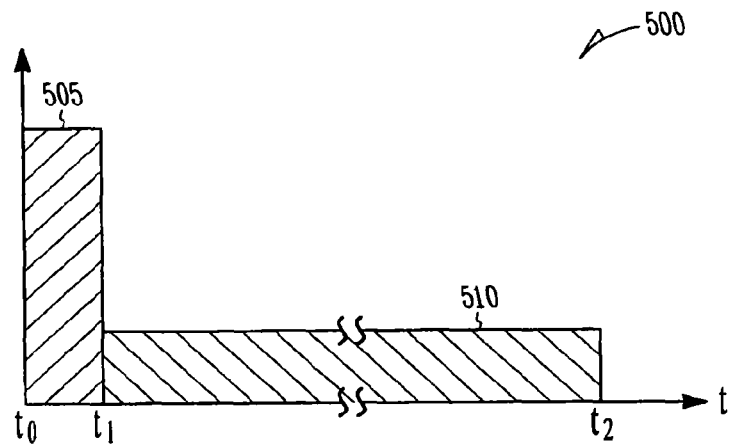
FIG. 5 illustrates a graph of an example of a combination meal bolus of insulin.

FIG. 5 illustrates a graph 500 of an example of a combination meal bolus of insulin. The graph 500 shows an amount of insulin delivered versus time. The combination meal bolus includes a first portion 505 of insulin that is delivered immediately beginning at time $t_0$. The first portion 505 concludes at time $t_1$ when a second portion 510 of insulin begins to be delivered. The second portion 510 is delivered over an extended period of time until time $t_2$. The extended portion is delivered at a lower rate and for a longer period of time than the first portion 505. The combination bolus may be timed by the insulin timing module 225 of FIG. 2. If abnormal gastric emptying is indicated for a user, the insulin timing module 225 may change the combination meal bolus.

Figure 6:
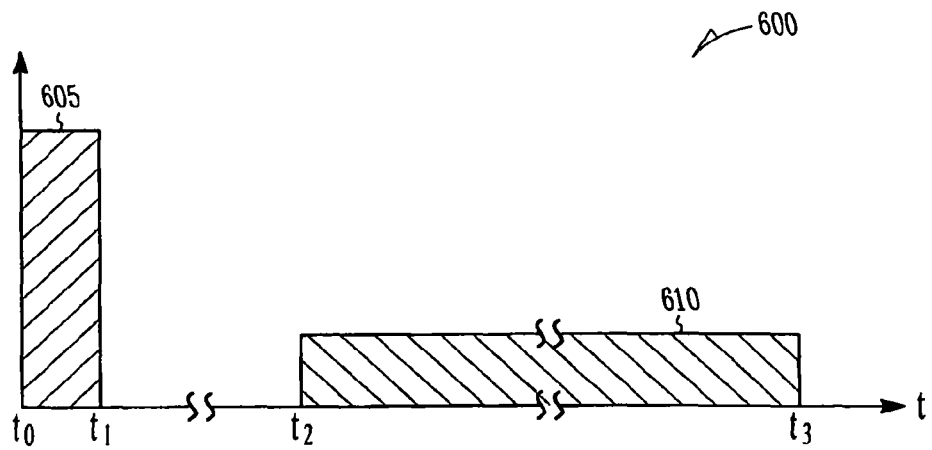
FIG. 6 illustrates a graph of another example of a combination meal bolus of insulin.

FIG. 6 illustrates a graph 600 of another example of a combination meal bolus of insulin. The combination meal bolus includes a first portion 605 of insulin and a second portion 610 of insulin. The first portion 605 is delivered immediately beginning at time $t_0$ and concludes at time $t_1$. If abnormal gastric emptying is indicated for the user, the insulin timing module 225 generates a delay between the first portion 605 and the second portion 610. The second portion is delivered beginning after the delay at time $t_2$ and concludes at time $t_3$.

According to some embodiments, the information related to managing diabetes of the user of the device 200 of FIG. 2 includes an indication of a drug the user is taking. The insulin timing module 225, in response to the indication, recommends at least one of a change in an amount of insulin delivered in a bolus, a change to a user's total daily dose of insulin, or a change in a frequency of blood glucose checks of the user.

For example, the information related to managing diabetes includes an indication that the user is taking a hormone to assist uptake of insulin (e.g., Symlin®). When such a hormone is indicated, the insulin timing module 225 may reduce the amount of insulin delivered in the meal bolus and may recommend a reduction in the user's total daily dose of insulin. In some embodiments, the insulin timing module 225 may deliver the meal bolus over an extended period of time (e.g., reduce the rate of the meal bolus but provide the bolus over a longer time, such as the extended second portion 510 in FIG. 5). In some embodiments, the insulin timing module 225 may deliver the meal bolus as a combination bolus that includes a first portion that is delivered immediately and a second portion that is delivered over an extended period.

In another example, the information related to managing diabetes includes an indication that the user is taking a beta-adrenergic blocking agent. Beta-adrenergic blocking agents may increase the chance of developing either high or low blood glucose levels and may cause a low blood glucose level to last longer than normal. If a beta-adrenergic blocking agent is indicated, the insulin timing module 225 may change the delivery of a meal bolus to counteract a likelihood of a high or low blood glucose level such as by changing the amount of insulin in the meal bolus or delivering the meal bolus as a combination bolus. Beta-adrenergic blocking agents also may cover up symptoms indicative of low blood sugar. For this reasons, the insulin timing module 225 may recommend an increase in blood glucose checks of the user.

In another example, the information related to managing diabetes includes an indication that the user is using a corticosteroid. Corticosteroids taken over several weeks such as by being applied to the skin for a long period of time or injected into a joint may increase the blood glucose level of the user. If a corticosteroid is indicated, the insulin timing module 225 may reduce the amount of insulin in a meal bolus.

In another example, the information related to managing diabetes includes an indication that the user has consumed some amount of alcohol. Such consumption can increase the effect of insulin to lower blood glucose. If alcohol consumption is indicated, the insulin timing module 225 may reduce the amount of insulin in a meal bolus.

According to some embodiments, the information related to managing diabetes of a user includes information related to the nutrient content of the meal eaten or anticipated to be eaten by the user. The controller 205 includes an insulin calculation module 240. Nutrient content includes an amount of fat, protein, fiber and/or carbohydrates in a meal. The insulin calculation module 240 calculates an amount of insulin to deliver in a meal bolus of insulin to cover an amount of carbohydrates in the meal using a carbohydrate ratio.

A carbohydrate ratio refers to the amount of carbohydrates covered by a unit of insulin. It is sometimes referred to as a carbohydrate factor, or carb factor, and is typically specified as grams of carbohydrates per unit of insulin. An insulin pump may use the carbohydrate ratio to automatically determine a carbohydrate insulin bolus amount required to match a number of carbohydrates ingested by the patient, or at least to keep post-meal blood glucose within a range that is healthy for a patient. For example, the patient may plan to eat 70 grams of carbohydrates. If the carbohydrate ratio is 10 grams of carbohydrates per unit of insulin (10 g/u), the insulin pump would determine that 7 units of insulin are required to cover the carbohydrates. An appropriate carbohydrate ratio may vary from person to person, yet it is important for a pump to use an appropriate carbohydrate ratio. Descriptions of systems, devices, and methods to automatically determine a carbohydrate ratio for an insulin pump user are found in Blomquist, "Carbohydrate Ratio Testing Using Frequent Blood Glucose Input," U.S. patent application Ser. No. 11/679,712, filed Feb. 27, 2007, which is incorporated herein by reference in its entirety.

In some embodiments, the insulin calculation module 240 calculates an amount of insulin to deliver in the meal bolus using an amount of protein indicated in the nutrient content of the meal and using a protein ratio. Similar to a carbohydrate ratio, a protein ratio refers to the amount of protein covered by a unit of insulin. In some embodiments, the insulin calculation module 240 calculates an amount of insulin to deliver in the meal bolus using an amount of fat indicated in the nutrient content of the meal and using a fat ratio. A fat ratio refers to the amount of fat covered by a unit of insulin. The insulin calculation module 240 adds the amount of insulin needed to cover the fat and/or protein to the amount of insulin calculated to cover the carbohydrates in order to determine the total meal bolus amount. In some embodiments, the insulin calculation module 240 calculates the amount of insulin to deliver by using the fiber content of the meal to adjust the bolus amount. Typically, the carbohydrate grams of the meal that are from un-metabolized fiber are subtracted from the total grams of carbohydrates eaten.

According to some embodiments, the insulin timing module 225 delivers a portion of a meal bolus at or near the beginning of a meal time period. The meal bolus may be scheduled by being pre-programmed into the device 200 or the user may enter the meal time through the user interface 215. The information related to managing diabetes of a user includes a nutrient content of the meal actually consumed. This information may be entered by the user at the end of a meal. If the nutrient content information indicates the partial meal bolus did not have enough insulin to cover the meal, the insulin calculation module 240 calculates a second portion of the meal bolus to cover the meal using the nutrient content information. For example, assume that carbohydrate ratio for the user is 20 grams of carbohydrates per unit of insulin (20 g/u). Assume the partial meal bolus contained one unit of insulin, or enough to cover 20 grams of carbohydrates. If the nutrient information indicates that the user consumed 50 grams of carbohydrates in the meal, the insulin calculation module 240 calculates that the second portion of the meal bolus should contain 1.5 units of insulin.

If the nutrient content information indicates the partial meal bolus had too much insulin to cover what was actually eaten, the insulin calculation module 240 calculates an amount of carbohydrates, to be consumed in addition to the meal, to cover the extra insulin. For example, again assume that carbohydrate ratio for the user is 20 grams of carbohydrates per unit of insulin (20 g/u) and the partial meal bolus contained one unit of insulin, or enough to cover 20 grams of carbohydrates. If the nutrient information indicates that the user only consumed 10 grams of carbohydrates in the meal, the insulin calculation module 240 calculates that user should consume 10 more grams of carbohydrates to cover the extra insulin in the partial meal bolus. The controller 205 may display a recommendation and/or generate an alert indication to the user to consume the additional carbohydrates.

The partial meal bolus feature is useful in a situation where the user orders meal but there is a delay between the time a meal bolus is given and the meal actually arrives. The user takes a partial meal bolus before the meal arrives. The user can then enter the amount of carbohydrates that are consumed or will be consumed, and the device calculates the remaining portion of the meal bolus to deliver. The feature is also useful in the situation where the insulin pump user is a child. A parent initiates a partial meal bolus for the child at meal time. The parent then enters the nutrient content information of the meal actually eaten by the child and the insulin calculation module 240 calculates the second portion of the meal bolus according to the information.

According to some embodiments, the nutrient content information includes an indication of an amount of fast absorbing carbohydrates. The information may also include and an amount of slow absorbing carbohydrates in the meal. The insulin calculation module 240 calculates an amount of insulin to deliver immediately in a first portion of a meal bolus using an amount of fast absorbing carbohydrates in the meal, and calculates an amount of insulin to deliver over an extended time period using an amount of slow absorbing carbohydrates in the meal, and/or an amount of fat in the meal, and/or an amount of protein in the meal. The meal bolus is delivered as a combination bolus such as those shown in FIGS. 5 and 6. The insulin timing module 225 may time the durations of the first and second bolus portions.

Automatic determination of an appropriate amount of insulin in the meal bolus can assist an insulin pump user in achieving better control of their blood glucose levels. As described above, the delivery of insulin in a time relation to a meal may be delivered as a change in a basal rate pattern or profile. According to some embodiments, the information related to managing diabetes of a user received by the input 220 includes a delivery pattern of basal insulin to be stored in a memory associated with the controller 205. The memory may be integral to the controller 205 or separate from the controller 205. The insulin timing module 225 shifts at least a portion of basal insulin normally delivered during a time period after the meal time to a time period prior to the meal time and decreases an amount of insulin delivered after the meal time period by the amount delivered prior to the meal.

Figure 7:
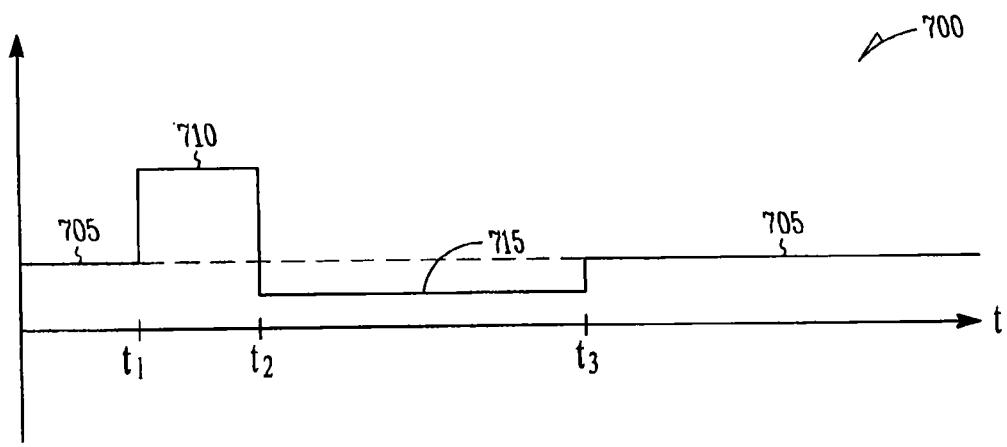
FIG. 7 illustrates a graph of an example of this basal insulin shifting.

FIG. 7 illustrates a graph 700 of an example of this basal insulin shifting. The graph 700 represents the rate of basal insulin delivered to the insulin pump user versus time. Prior to a meal time, basal insulin is delivered at a first rate 705. As the scheduled meal time approaches, the insulin timing module 225 increases the basal rate at time $t_1$ to a second rate 710. At a time $t_2$ after the meal, the insulin timing module 225 decreases the basal rate to a third rate 715. The device 200 delivers insulin at the third rate 715 until time $t_3$. After time $t_3$, insulin is delivered at the first basal rate 705. In some embodiments, the amount of increase in insulin delivered during interval $t_1$-$t_2$ is substantially the same as the amount of decrease in insulin delivered during time $t_2$-$t_3$.

In some embodiments, the insulin timing module 225 shifts all of the basal insulin to be delivered during a two to three hour period after a meal time to the hour immediately preceding the meal time. After the meal time, the insulin timing module 225 may suspend delivery of basal insulin until all basal insulin that was shifted to a time prior to the meal would have been delivered by the un-shifted basal delivery pattern. In FIG. 7, this would increase the amount of insulin delivered during interval $t_1$-$t_2$ and reduce the amount of insulin delivered during time $t_2$-$t_3$ to zero.

In some embodiments, the meal times are programmed or scheduled into the device 200 of FIG. 2, or the device 200 may deduce when meal times occur from missed meal bolus alerts programmed into the device. A missed meal bolus alert may be issued by the device 200 when no meal bolus was delivered by the device 200 at a specified time. Because the meal bolus is delivered before a meal time, the device can deduce the meal time. In some embodiments, the device 200 provides an alert to the user of the shifted basal rate pattern before delivering insulin according to the new pattern. The alert may in the form of an alarm or a display. The user then activates the shifted delivery pattern of basal insulin according to a user response received via the user interface 215.

Figure 8:
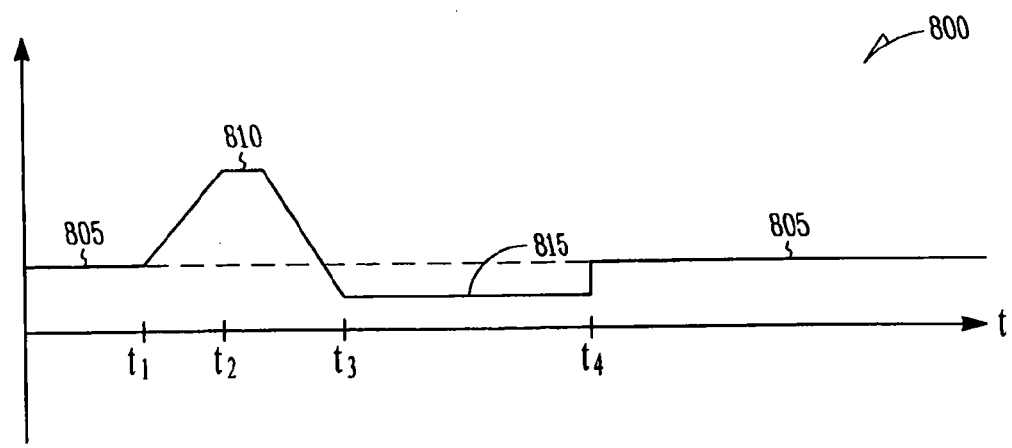
FIG. 8 illustrates a graph of an example of basal insulin delivered at a ramped rate.

In some embodiments, the insulin timing module 225 ramps the rate at which the basal insulin is delivered prior to the meal time period. An example is shown in the graph 800 of FIG. 8. Prior to a meal time, basal insulin is delivered at a first rate 805. As the scheduled meal time approaches, the insulin timing module 225 ramps the basal rate beginning at time $t_1$ up to a second rate 810 at time $t_2$. After the meal, the insulin timing module 225 decreases the basal rate to a third rate 815. In some embodiments, the insulin timing module 225 ramps the basal rate down to the third rate 815 until time $t_3$. The device 200 delivers insulin at the third rate 815 until time $t_4$. After time $t_3$, insulin is delivered at the first basal rate 805. In some embodiments, the amount of increase in insulin delivered during interval $t_1$-$t_3$ is substantially the same as the amount of decrease in insulin delivered during time $t_3$-$t_4$.

Avoiding Alarm Fatigue

An insulin pump may provide an alarm or other kind of alert to prompt the user to do certain actions that help ensure the user is making effective use of their pump. These alerts may include a reminder to the user to initiate a blood glucose measurement. Recurrent blood glucose measurements may be necessary to give a patient a good overall view of their blood glucose management. An alert to measure blood glucose may be generated a timed interval after a meal, after a correction bolus has been delivered, or after the user has had a high or low blood glucose reading. Because it is optional for the user to test their blood glucose when these alerts occur, many users get in the habit of routinely canceling the alert and not checking their blood glucose. This is sometimes referred to as alarm fatigue. Thus, it is desirable to make it more difficult or less likely for the user to ignore the alert.

Figure 9:
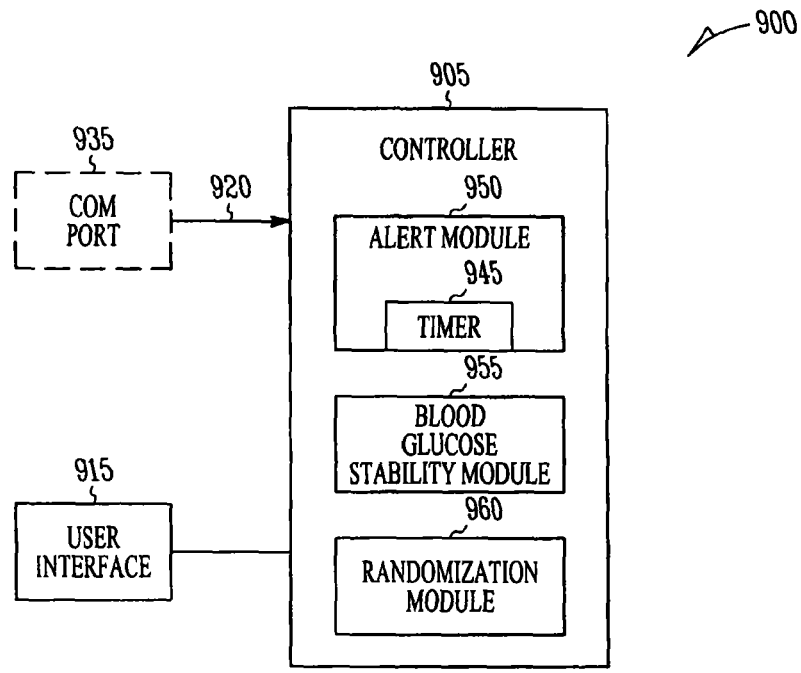
FIG. 9 is a block diagram of portions of an embodiment of a blood glucose (BG) management device to reduce alarm fatigue.

FIG. 9 is a block diagram of portions of an embodiment of a blood glucose (BG) management device 900 to reduce alarm fatigue. The device 900 includes a controller 905 communicatively coupled to a user interface 915 and an input 920. The input 920 receives blood glucose information into the device 900. The information includes a blood glucose level of the user. The controller 905 includes an alert module 950 to provide an alert to the user via the user interface 915. The alert notifies the user to check their blood glucose level.

The controller 905 also includes a blood glucose stability module 955 to calculate a measure of a past stability of the blood glucose level of the user using at least a portion of past blood glucose levels. In some embodiments, the blood glucose stability module 955 trends the measure. In some embodiments, the blood glucose stability module 955 measures a central tendency of the blood glucose level of the user, such as an average blood glucose value or a median blood glucose value for example. In some embodiments, the blood glucose stability module 955 measures a maximum blood glucose level of the user. In some embodiments, the blood glucose stability module 955 measures a minimum blood glucose level of the user. In some embodiments, the blood glucose stability module 955 measures a standard deviation of the blood glucose level of the user.

The controller 905 also includes a randomization module 960. According to the measure of the past blood glucose stability, the randomization module 960 randomizes the alert function of the device 900. For example, the randomization module 960 may set the likelihood of the device 900 generating an alarm based on the historical stability of the blood glucose level of the user. Users that have stable blood glucose levels are rewarded with fewer alerts to check their blood glucose level.

The randomization module 960 may randomize a type of alert to provide or may randomize whether to provide the alert to the user at all. For example, the device 900 may randomize whether to generate a Check Blood Glucose alarm after eating or after taking a correction bolus. The randomization module 960 may randomize a method needed to deactivate an alert or alarm by randomizing a user input to the user interface 915 needed to reset a provided alert.

In some embodiments, the alert module 950 includes a timer 945, and the alert module 950 provides an alert a timed duration after the blood glucose information indicates that the blood glucose level of the user differs from a target blood glucose level by a threshold value. In some embodiments, the device 900 includes a communication port 935 coupled to the input 920 and the communication port configured to receive the blood glucose information from a second separate device. For example, the second device may be a blood glucose monitor, or a device that communicates blood glucose information received from a blood glucose monitor. In some embodiments, the communication port 935 is a wireless port such as an IR port or an RF port. In some embodiments, the communication port 935 is a wired port, such as a serial port for example.

Figure 10:
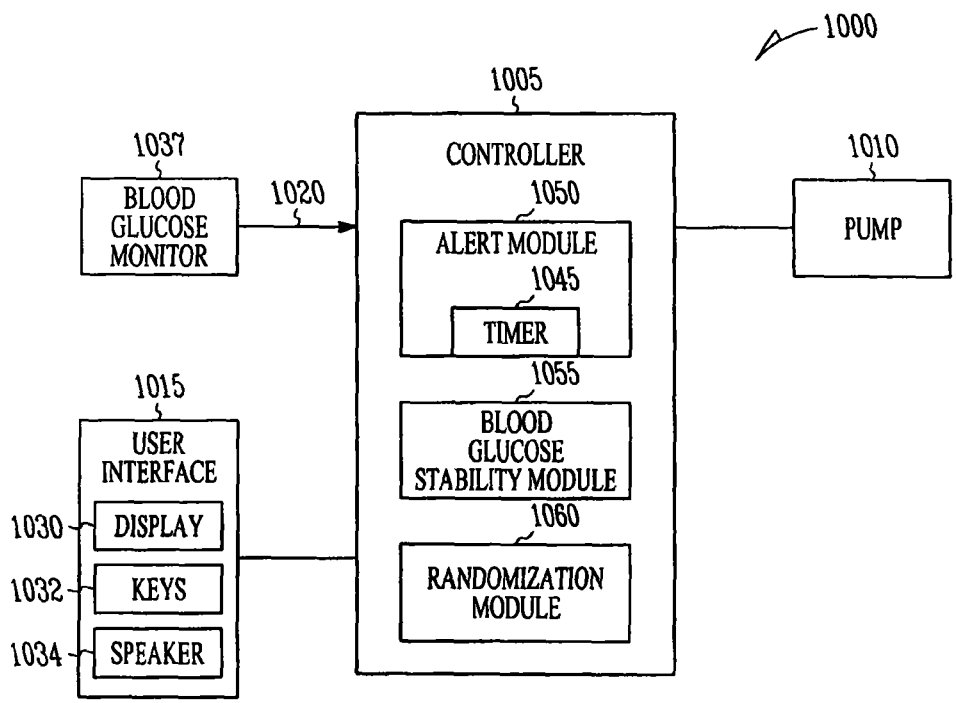
FIG. 10 is a block diagram of portions of another embodiment of a BG management device to reduce alarm fatigue.

FIG. 10 is a block diagram of portions of another embodiment of a BG management device 1000 to reduce alarm fatigue. The device 1000 includes a controller 1005, a user interface 1015, and an input 1020. The controller 1005 includes an alert module 1050, a blood glucose stability module 1055, and a randomization module 1060. In some embodiments, the user interface 1015 includes a display 1030 and the alert module 1050 provides the alert through the display 1030. In some embodiments, the user interface 1015 includes a speaker 1034, and the randomization module 1060 randomizes an audible indication of an alert, or an audible aspect of the alert, via the user interface 1015. In some embodiments, the randomization module 1060 randomizes whether the alert is visual or audible. In some embodiments, the user interface 1015 includes a plurality of keys 1032 to be pressed by a user of the device 1000. The randomization module 1060 randomizes a sequence of key presses needed to reset a generated alert.

According to some embodiments, the BG management device 1000 is an insulin pump and includes a pump 1010 to deliver insulin. The alert module 1050 includes a timer 1045 and the alert module is configured to provide an alert (e.g., to check the blood glucose level) a timed duration after delivery of a bolus of insulin.

According to some embodiments, the BG management device 1000 includes a blood glucose monitor 1037 communicatively coupled to the input 1020 and the input 1020 receives the blood glucose information from the blood glucose monitor. In some embodiments, the user interface 1015 is configured to receive manual entry of the blood glucose information from the user. In some embodiments, the user interface 1015 includes a display 1030. The controller 1005 prompts the user, via the display 1030, to begin a blood glucose measurement using a second separate device.

Figure 11:
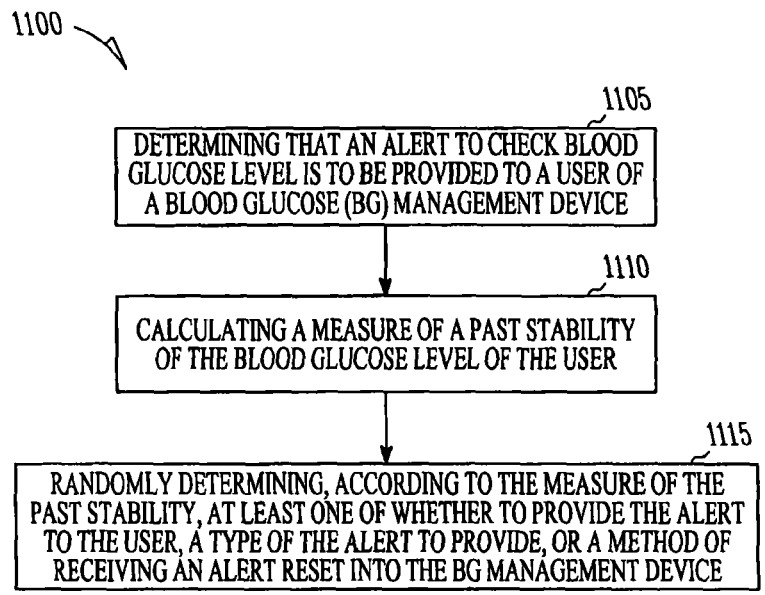
FIG. 11 is a flow diagram of a method of reducing alarm fatigue in a BG management device.

FIG. 11 is a flow diagram of a method 1100 of reducing alarm fatigue in a BG management device. At block 1105, it is determined that an alert to check blood glucose level is to be provided to a user of the BG management device. This may be because the device determines the blood glucose level of the device user differs from a target blood glucose level by more than a specified threshold value. At block 1110, a measure of a past stability of the blood glucose level of the user is calculated by the BG management device.

At block 1115, the device randomly determines, according to the measure of the past stability, at least one of whether to provide the alert to the user, a type of the alert to provide, or a method of receiving an alert reset into the BG management device. Randomly changing the tone or changing the key input needed to cancel the alarm or alert makes it less likely the user will cancel the alarm out of habit and makes it more likely to use the alert feature.

Scoring Insulin Pump Use

It would be helpful to an insulin pump user if the insulin pump were able to communicate how well the person was using the device, and to communicate advice on how to improve their use. This may increase efficacy of the pump and thereby increase the benefit to the patient.

Figure 12:
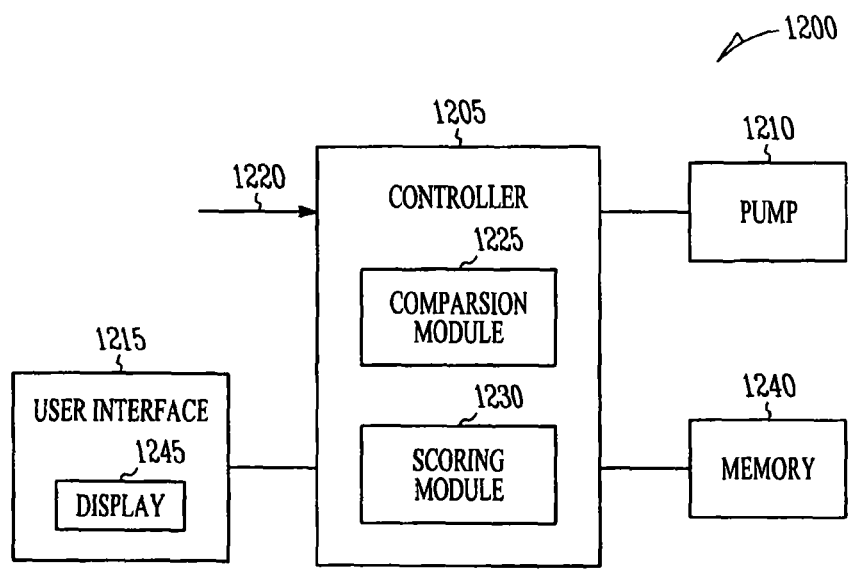
FIG. 12 is a block diagram of portions of an embodiment of a device that helps a patient improve their use of an insulin pump.

FIG. 12 is a block diagram of portions of an embodiment of a device 1200 that helps a patient improve their use of an insulin pump included in the device 1200. The device 1200 includes a controller 1205 communicatively coupled to a pump 1210 to deliver insulin, a user interface 1215, and a memory 1240. The memory 1240 is to store guideline parameters related to use of the device 1200. The guideline parameters are ideal parameters, or range of values for a parameter, that an insulin pump user would meet if the user were making the best use of their insulin pump. The guideline parameters may include default parameters and/or include parameters programmed into the device 1200 by a diabetes professional. The programming may be done using the user interface 1215 or by communicating with the device 1200 using a second separate device via a communication port coupled to the input 1220. Examples of parameters include parameters related to the user checking their blood glucose, parameters related to insulin cartridge use, parameters related to the dietary habits of the user, and parameters related to using the features of the insulin pump.

The controller 1205 includes a comparison module 1225 and a scoring module 1230. The comparison module 1225 monitors the patient's use of the device 1200 and compares parameters related to the patient's use to the guideline parameters stored in memory 1240. The scoring module 1230 calculates a score based on the monitored patient use and is indicative of the efficacy of the patient's insulin pump use. The score reflects how well the patient is following best practices for insulin pump users. Based on the score, the controller 1205 communicates advice to the user on how to increase pump efficacy (e.g., how to bring the values of the patient's use parameters toward the guideline parameter values). A higher score indicates that the patient is following guidelines established by their health care provider (e.g., a diabetes professional) and indicates the patient is following best practice in controlling their blood glucose.

In some embodiments, the user interface 1215 includes a display 1245. The controller 1205 may prompt the user, via the display, to begin a blood glucose measurement using a separate device. The user interface 1215 may include keys for receiving manual entry of the blood glucose information into the device from the user.

According to some embodiments, the stored guideline parameters are related to a user entering blood glucose readings into the device 1200. In some embodiments, the stored guideline parameters include the frequency with which blood glucose readings are entered into the device. The comparison module 1225 records (e.g., stores) and compares the frequency with which blood glucose readings are entered into the device 1200 by a user to the guideline frequency stored in memory. The scoring module 1230 determines a score based on how closely the user's frequency of entering readings matches the guideline frequency. In some embodiments, the stored guideline parameters include the timing of the blood glucose readings. For example, the guideline parameters may specify one or more times of day that the user is to enter a blood glucose reading. The comparison module 1225 compares the actual times the user enters blood glucose readings to the stored parameter guideline times, and the scoring module 1230 determines a score based on how closely the user's times match the guideline times.

According to some embodiments, the stored guideline parameters are related to the dietary habits of the user. In some embodiments, the stored guideline parameters include an amount of carbohydrates, such as a guideline amount for the user to eat during a scheduled meal for example. The comparison module 1225 compares the amount of carbohydrates, entered into the device 1200 as having been eaten by the user, to the stored guideline amount of carbohydrates. In some embodiments, the stored guideline parameters include a number of between meal snacks. The comparison module 1225 compares the number of between meal snacks, entered into the device 1200 as having been eaten by the user, to a stored guideline number of between meal snacks. The scoring module 1230 scores the dietary habits of the user accordingly.

In some embodiments, the stored guideline parameters include a difference value in the timing of patient meal times. The comparison module 1225 compares actual meal times entered into the device 1200 by a user to scheduled meal times and determines any differences in the meal times. The comparison module 1225 then compares to one or more time difference values in the meal times to the stored guideline meal time difference value. The scoring module 1230 assigns a higher score for consistency in meal times higher than for a large variation in meal times. In some embodiments, the stored guideline parameters include the frequency with which a user fails to initiate a meal bolus before eating. The comparison module records whether a user fails to take a meal bolus before eating. The comparison module 1225 compares the frequency that meal boluses are missed to a stored guideline value for an allowed frequency of missed meal boluses. The scoring module 1230 generates a lower score for more missed meal boluses.

According to some embodiments, the stored guideline parameters are related to insulin cartridge use and/or infusion set use. In some embodiments, the stored guideline parameters include the frequency with which the user changes insulin cartridges. The device 1200 may include a circuit to detect when the cartridge is changed. The comparison module 1225 compares the frequency of actual cartridge changes by a user to the stored guideline insulin cartridge change frequency value. The scoring module 1230 generates higher score for how closely the user's frequency of changes matches the stored guideline. Not changing the insulin cartridge often enough risks insulin clotting or losing effectiveness of the insulin due to exposure to higher temperatures.

In some embodiments, the stored guideline parameters include the frequency with which the user changes infusion sets. The comparison module 1225 compares the frequency of actual infusion set changes as indicated by a user to the stored guideline infusion set change frequency value. The scoring module 1230 generates higher score for how closely the user's frequency of actual infusion set changes matches the stored guideline. Not changing the infusion set often enough may result in infections.

In some embodiments, the stored guideline is the frequency that insulin cartridges for the device 1200 become empty, thereby interrupting therapy. The comparison module 1225 compares the frequency that the user allows insulin cartridges to empty to the stored guideline frequency value.

Allowing insulin cartridges to empty often may indicate that the user is not paying proper attention to their device 1200 and the scoring module 1230 provides a higher score the closer the actual frequency that insulin cartridges become empty matches the guideline frequency. In some embodiments, the stored guideline parameters include the difference in timing between insulin cartridge changes. The comparison module 1225 compares the difference in times between insulin cartridge changes to a stored guideline difference value. The scoring module 1230 would score consistency in insulin cartridge changes higher than a large variation in time between insulin cartridge changes.

According to some embodiments, the stored guideline parameters are related to use of the features of the device 1200. In some embodiments, the stored guideline parameters include the frequency that a user uses the test features of the device 1200. For example, the device 1200 may include a carbohydrate ratio test feature. Descriptions of devices and methods that perform a carbohydrate ratio test are found in Blomquist, "Carbohydrate Ratio Testing Using Frequent Blood Glucose Input," U.S. patent application Ser. No. 11/679,712, filed Feb. 27, 2007, which is incorporated herein by reference in its entirety. The device 1200 may include a basal rate test feature. Descriptions of devices and methods that perform a basal rate test are found in Blomquist et al., "Basal Rate Testing Using Frequent Blood Glucose Input," U.S. patent application Ser. No. 11/685,617, filed Mar. 13, 2007, which is incorporated herein by reference in its entirety. The device 1200 may include a correction factor test feature. Descriptions of devices and methods that perform a correction factor test are found in Blomquist et al., "Correction Factor Testing Using Frequent Blood Glucose Input," U.S. patent application Ser. No. 11/626,653, filed Jan. 24, 2007, which is incorporated herein by reference in its entirety. The comparison module 1225 compares the frequency with which a user uses a test feature of the device 1200 and compares the frequency to a stored guideline device test frequency value. The scoring module 1230 generates a higher score if the user uses the test features more often.

In some embodiments, the device 1200 includes a feature that generates a device report. The controller 1205 is configured to store events in the memory 1240. Examples of such events include historical insulin delivery information and recorded use parameters. In some embodiments, the controller 1205 displays the report using a display 1245 included in the device 1200. In some embodiments, device 1200 includes communication port and the controller 1205 communicates information to a second separate device via the communication port for formatting and display or printing of the report. The stored guideline parameters include the frequency with which a user views a generated report. The comparison module 1225 compares the frequency with which a user views a pump generated report to a stored report-view frequency value.

In some embodiments, the device includes one or more alert features. These alerts may include a reminder to the user to initiate a blood glucose measurement (e.g., after a meal of after a correction bolus), or after the user has had a high or low blood glucose reading. The user interface 1215 may include a display 1245 to provide a visual alert, a speaker or transducer to provide an audible alert, and/or a mechanism to provide a vibratory alert.

In some embodiments, the stored guideline parameters include an alert response time. The comparison module 1225 determines the time from when an alert is generated by the device 1200 to the time when the user responds to the alert. The comparison module 1225 compares the user response time to the stored guideline response time value. The scoring module 1230 generates a higher score if the user's response times are within the guideline response time. In some embodiments, the stored guideline parameters include the total time that the device 1200 may be inoperative. The comparison module 1225 compares the total time that a user renders the device 1200 inoperative to the guideline time. The scoring module 1230 generates a higher score the more often the user uses the device 1200.

In some embodiments, the device 1200 includes an input 1220. Blood glucose information is received into the device 1200 via the input 1220. The blood glucose information may include one or more blood glucose levels of the user. In some embodiments, the device 1200 includes a blood glucose monitor communicatively coupled to the input 1220. The blood glucose monitor may be communicatively coupled via a wireless port or a wired port. The blood glucose monitor may be a continuous blood glucose monitor. In some embodiments, the device 1200 includes a communication port coupled to the input 1220 and configured to receive blood glucose information from a second separate device. The communication port may be a wireless communication port (e.g., IR or RF) or may be a wired port (e.g., a serial port).

The comparison module 1225 monitors the blood glucose level of the patient using the information. In some embodiments, the comparison module 1225 determines and monitors a central tendency of the blood glucose level of the user from the information, such as the average value or median value for example. In some embodiments, the comparison module 1225 uses the blood glucose information to determine and monitor a standard deviation of the user's blood glucose level. In some embodiments, the comparison module 1225 uses the blood glucose information to determine and monitor an amount of insulin delivered in any correction boluses as a percentage of TDD. As described previously, the input 1220 may be communicatively coupled to the input and the blood glucose information is received by manual entry of the information into the device 1200.

According to some embodiments, the stored guideline parameters are related to the user's management of their blood glucose level. In some embodiments, the stored guideline parameters may include a number of times that the user is allowed to neglect taking a correction bolus when the blood glucose information indicates that the blood glucose of the patient exceeds a target blood glucose level by a threshold value. Of course, the stored number of times may be zero. The comparison module 1225 compares the number of times that the patient did not initiate a correction bolus to the stored guideline number of times. The scoring module 1230 generates a higher score the closer the actual number is to the stored number.

In some embodiments, the stored guideline parameters are related to the user's rechecking their blood glucose some interval after receiving a correction bolus, or some interval after treating a low blood glucose level. The comparison module 1225 compares the number of times that the patient failed to recheck their blood glucose to the stored guideline number of times. In some embodiments, the stored guideline parameters include a number of times that the user is allowed to neglect to recheck blood glucose after a bolus of insulin is delivered by the device 1200. The comparison module 1225 compares the number of times that the patient failed to recheck their blood glucose to the stored guideline number of times. The scoring module 1230 generates a higher score the closer the actual number is to the stored number.

According to some embodiments, the scoring module 1230 trends the calculated score. The controller 1205 may display the score and/or the score trend on the display 1245 when prompted to do so (e.g., through the user interface 1215). Such a trend may be included in a device-generated report. When calculating the score, the scoring module 1230 assign different weights to outcomes of the comparisons described. For example, the scoring module may assign a higher weight to the user making consistent blood glucose measurements higher than the user using test features of the device.

The controller 1205 communicates advice to the user on how to increase pump efficacy based on the calculated score. For example, if the controller 1205 determines that there is a poor score for taking meal boluses, the controller 1205 may display to the user that the patient's overall use of the device may be improved by paying more attention to meal boluses. In some embodiments, the device 1200 includes a communication port and the advice on how to increase pump efficacy is communicated to a second separate device.

In some embodiments, the scoring can be implemented into a game. This may be useful to encourage young insulin pump users (e.g., children) to become interested in learning about their pump. The score may be communicated to a second separate device (e.g., a computer). The second device could print certificates when the user meets or exceeds one or more threshold scores. The device 1200 or the second device can offer advice on how to increase the pump user's score. The certificates could be redeemable (e.g., by the manufacturer).

Figure 13:
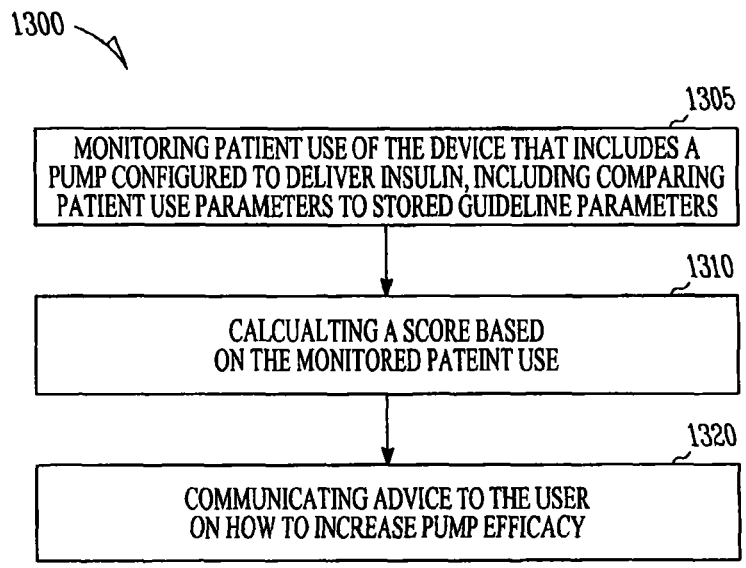
FIG. 13 is a flow diagram of a method of using a medical device to help a patient improve their use of an insulin pump.

FIG. 13 is a flow diagram of a method 1300 of helping a patient improve their use of the insulin pump using a medical device. At block 1305, patient use of a device is monitored. The device includes a pump configured to deliver insulin. The patient use may be monitored using the insulin pump device, and the monitoring includes comparing patient use parameters to stored guideline parameters. Examples of the parameters include parameters related to a user entering blood glucose readings into the insulin pump, parameters related to the dietary habits of the user, parameters related to insulin cartridge use, parameters related to use of the features of the insulin pump, and parameters related to the user's management of their blood glucose level.

At block 1310, the medical device calculates a score based on the monitored patient use. The medical device may weigh some parameters higher than others when calculating the score. At block 1315, advice is communicated to the user or patient on how to increase pump efficacy.

Shifting Insulin Therapy Parameters in Time

An insulin pump provides insulin therapy to a user using one or more delivery parameters. An example of such a parameter is a basal rate pattern. Basal rate refers to a type of twenty-four hour background infusion of insulin by an insulin pump that mimics the continuous background release of insulin from a normal pancreas. It is the rate of insulin delivery the patient normally needs independent of the consumption of meals. The basal rate is typically specified in insulin units per hour (u/hr). The variation in the rate as a function of time can be referred to as a basal rate pattern or profile. Sometimes it is desirable to vary the basal rate pattern throughout the day to deliver a different basal rate according to a patient's needs, such as delivering basal insulin at a different rate when the insulin pump user is sleeping than when the user is awake. Other parameters may also have different optimum values at different times of the day.

A change in the user's schedule may cause the appropriate values of the delivery parameters to change. If the pump user travels and crosses time zones, their circadian clock doesn't immediately adjust to the new time, because, as with jet lag, it takes time for the user's body to adjust. Consequently, the delivery parameters may no longer be programmed appropriately. If the user adjusts the clock on their insulin pump to match the new time zone, they will instantly adjust their basal rate pattern to the new time. This may not be appropriate because the user's body clock will be expecting basal insulin according to the old time zone. For example, if the user travels from the Pacific Time Zone to the Eastern Time Zone and adjusts the clock on their insulin pump three hours later, extra basal insulin scheduled for delivery at 2:00 AM will be delivered at 2:00 AM in the Eastern Time Zone while the user's body clock acts as though it is still 11:00 PM.

A better approach would be to not instantly shift the basal rate pattern to the new time when the insulin pump clock is adjusted. Instead the basal rate pattern should be gradually shifted (e.g., once per day) until the basal rate pattern was synchronized to the local time. A similar adjustment would be made on the return home to the original time zone. On a short trip, the basal rate pattern may not be fully adjusted to the new time. Additionally, the basal rate pattern could be gradually adjusted anytime the clock on the insulin pump was changed, such as during a change to or from daylight savings time.

Figure 14:
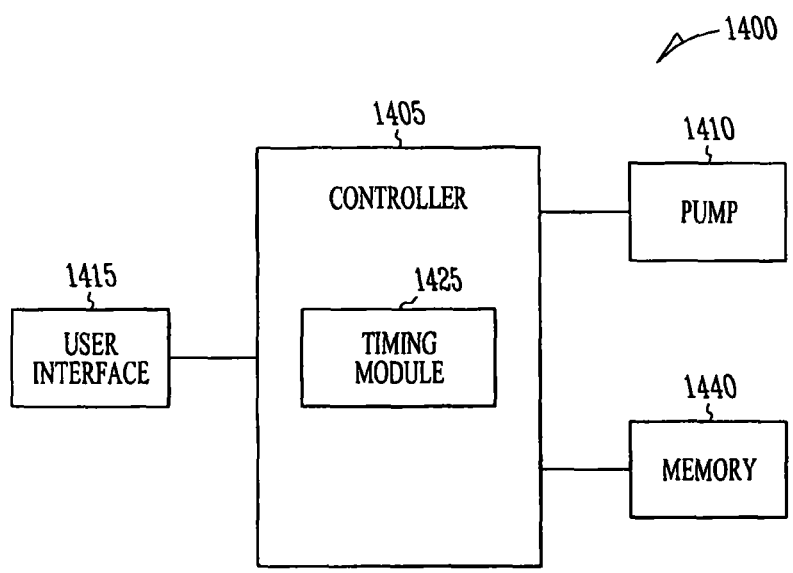
FIG. 14 is a block diagram of portions of an embodiment of a device that shifts insulin delivery parameters according to a change in the schedule of a user.

FIG. 14 is a block diagram of portions of an embodiment of a device 1400 that shifts insulin delivery parameters according to a change in the schedule of a user of the device 1400. The device 1400 includes a controller 1405 communicatively coupled to a pump 1410 configured to deliver insulin, a user interface 1415, and a memory 1440. The memory 1440 stores a delivery pattern of basal insulin. Time change information is received into the device 1400 through the user interface 1415. The user interface 1415 may include one or more keys or buttons for the user to enter the time change information. The controller 1405 includes a timing module 1425 configured to shift the delivery pattern of basal insulin in time according to the received information.

In some embodiments, the time change information includes travel information of the user. The travel information may include a destination of the user, or only the change in time zones the travel will involve. The travel information may include a travel departure time and travel return time. The timing module 1425 shifts the delivery pattern of basal insulin in time according to a destination time zone indicated in the travel information, and may restore the delivery pattern to its original time based on the travel return time. For example, in some people there is a "dawn phenomenon" where extra insulin is needed near 1 AM or 2 AM. Such a person may have a basal rate pattern that increases at that time. If the user travels from the Eastern Time Zone to the Pacific Time Zone, the timing module 1425 shifts the delivery pattern of basal insulin three hours later. Thus, if the basal rate pattern includes the increase during the early morning hours, the timing module 1425 would shift the increase later in time by three hours. If the travel information includes a return time, the timing module 1425 would shift the back to the original time three hours earlier upon the return time.

In some embodiments, the timing module 1425 shifts the delivery pattern of basal insulin by a specified amount of time per time period (e.g., by a fraction of an hour once per day, or a number of hours once per day) until the delivery pattern matches the destination time zone, and shifts the delivery pattern of basal insulin back by the same or a different amount of time until the delivery pattern matches the return time zone according to the return time. For example, if the user travels from the Eastern Time Zone to the Pacific Time Zone, the timing module 1425 shifts the delivery pattern of basal insulin by one-half hour per day until the delivery pattern is shifted three hours later. When the user returns as indicated by the return time or by an indication provided by the user via the user interface, the timing module 1425 begins shifting the delivery pattern earlier by a specified amount of time (e.g., the half hour once per day in the example) until the delivery pattern return to its original time.

In some embodiments, the time change information includes a change in local time, such as a change to or from daylight savings time. The timing module 1425 shifts the delivery pattern by a specified amount of time per time period until the delivery pattern matches the time change.

In some embodiments, the memory 1440 includes an indication of a sleep segment of the basal insulin delivery pattern. For example, the delivery pattern may repeat every twenty-four hours and a portion of the twenty-four hour period is designated as a sleep segment. Based on the time change information, the timing module 1425 shifts the sleep segment of the basal insulin delivery pattern.

According to some embodiments, the memory 1440 also stores other parameters related to the delivery of insulin. The controller 1405 may be configured (e.g., by programming) to change the value of these parameters according to the time of day. The insulin therapy for the user may improve by shifting these parameters in time according to a change in schedule of the user (e.g., due to travel). In some embodiments, the device 1400 may use a different correction factor at a different time of the day according to a time of day schedule. The timing module 1425 may shift the time of day schedule for the correction factor according to the time change information received into the device 1400 and stored in the memory 1440. In some embodiments, the device 1400 may use a different carbohydrate ratio at a different time of the day according to a time of day schedule. The timing module 1425 may shift the time of day schedule for the correction factor according to the travel information received into the device 1400.

Figure 15:
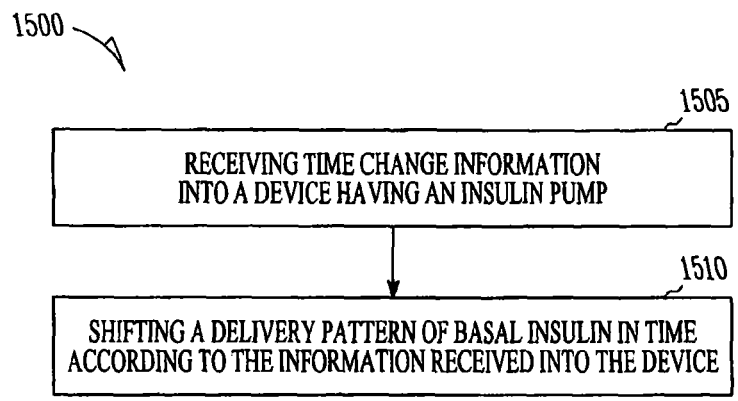
FIG. 15 is a flow diagram of an embodiment of a method to shift insulin delivery parameters according to a change in the schedule of a user of an insulin pump.

FIG. 15 is a flow diagram of an embodiment of a method 1500 to shift insulin delivery parameters according to a change in the schedule of a user of an insulin pump. At block 1505, information is received into a device having an insulin pump. The information may relate to local time change of a user of the insulin pump. At block 1510, the insulin pump device automatically shifts a delivery pattern of basal insulin in time according to the information received into the device. This insulin pump device may be configured to automatically make the shift by logic circuitry implemented in the device. The logic circuitry may include hardware, firmware, or software or any combination of hardware, firmware, or software.

Auto-Adjustment of Blood Glucose Testing Time

Proper management of blood glucose by insulin pump users includes periodic measurement of the user's blood glucose. For example, this may involve the user taking a blood glucose measurement to determine whether a correction bolus is needed or whether a meal bolus was effective. Testing blood glucose at proper times may give the patient a more accurate picture of their blood glucose control. This can be done by determining statistically significant, or historically significant, blood glucose sampling times and prompting the patient to measure their blood glucose at these times will give the patient that more accurate picture of their blood glucose control.

Figure 16:
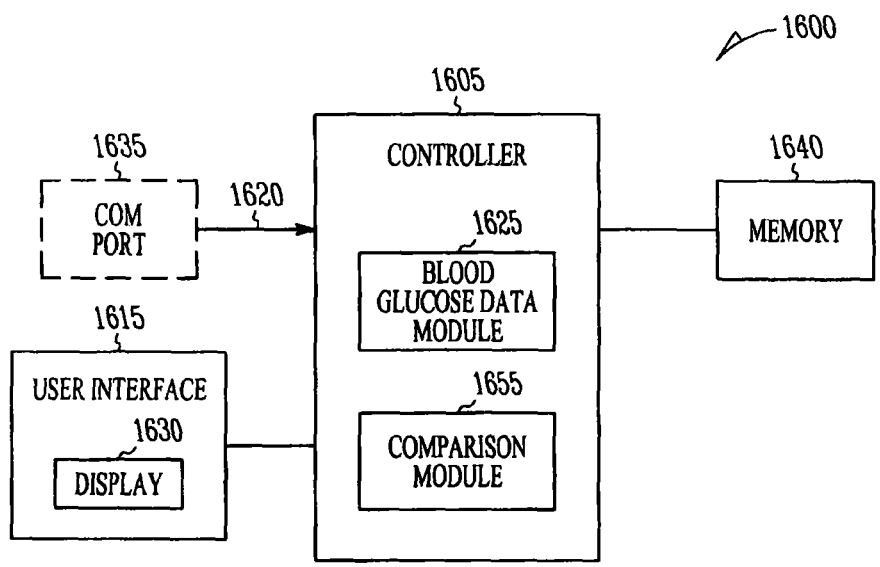
FIG. 16 is a block diagram of portions of an embodiment of a device to determine blood glucose testing times for an insulin pump user.

FIG. 16 is a block diagram of portions of an embodiment of a device 1600 to automatically determine blood glucose testing times for an insulin pump user. The device 1600 includes a controller 1605 communicatively coupled to a user interface 1615 and an input 1620. The input 1620 receives blood glucose data of the insulin pump user into the device 1600. The blood glucose data is obtained during a number of specified blood glucose testing times. The controller 1605 includes a blood glucose data module 1625.

The blood glucose data module 1625 calculates a measure of the user's blood glucose variability from the blood glucose data. In some embodiments, the blood glucose data module calculates a measure of statistical variability of the user's blood glucose such as one or more of a standard deviation of the blood glucose data, an average deviation of the blood glucose data, a variance of the blood glucose data, or a range of the blood glucose data. The controller 1605 adjusts a blood glucose testing time in response to the measure of blood glucose variability. For example, the measure of blood glucose variability may indicate that the user's blood glucose level is stable at certain times of the day and varies at other times of the day. The controller 1605 automatically adjusts one or more testing times to cover the period of greater variability.

In some embodiments, the device 1600 includes a display 1630. The controller 1605 prompts the user, via the display 1630, to initiate a blood glucose test. In some embodiments, the device includes a speaker or transducer communicatively coupled to the controller 1605 and provides an audible prompt to the user. The controller 1605 adjusts the blood glucose testing times by changing the times that it prompts the user to initiate a test.

According to some embodiments, the controller 1605 includes a comparison module 1655. The comparison module 1655 compares the measure of blood glucose variability to a threshold blood glucose variability value. The controller 1605 increases the number of blood glucose testing times if the measure of blood glucose variability exceeds a blood glucose variability target value by more than a first threshold blood glucose variability value. The controller 1605 decreases the number of blood glucose testing times if the measure of blood glucose variability is less than the blood glucose variability target value by more than a second threshold blood glucose variability value. This rewards the user with less testing times if the user is managing to keep their blood glucose relatively stable at a normal level.

In some embodiments, the device 1600 includes a memory 1640 communicatively coupled to the controller 1605. The memory 1640 stores an indication of a user preference for a blood glucose testing time. The controller 1600 adjusts the blood glucose testing time according to the indication. The indication may specify that fewer tests be requested by the device 1600 during certain times of the day. For example, the patient may specify that the device 1600 may request no more than two tests per week between the hours of 11:30 PM and 6:00 AM. The indication may be programmed into the device via the user interface 1615. The device 1600 limits the request for a blood glucose test as indicated even though the blood glucose data may show significant variation during that time.

In some embodiments, the controller 1605 creates or updates a schedule of a plurality of blood glucose testing times according to the patient indication and/or the measure of blood glucose variability provided by the blood glucose data module 1625. The schedule may be stored in memory 1640.

Figure 17:
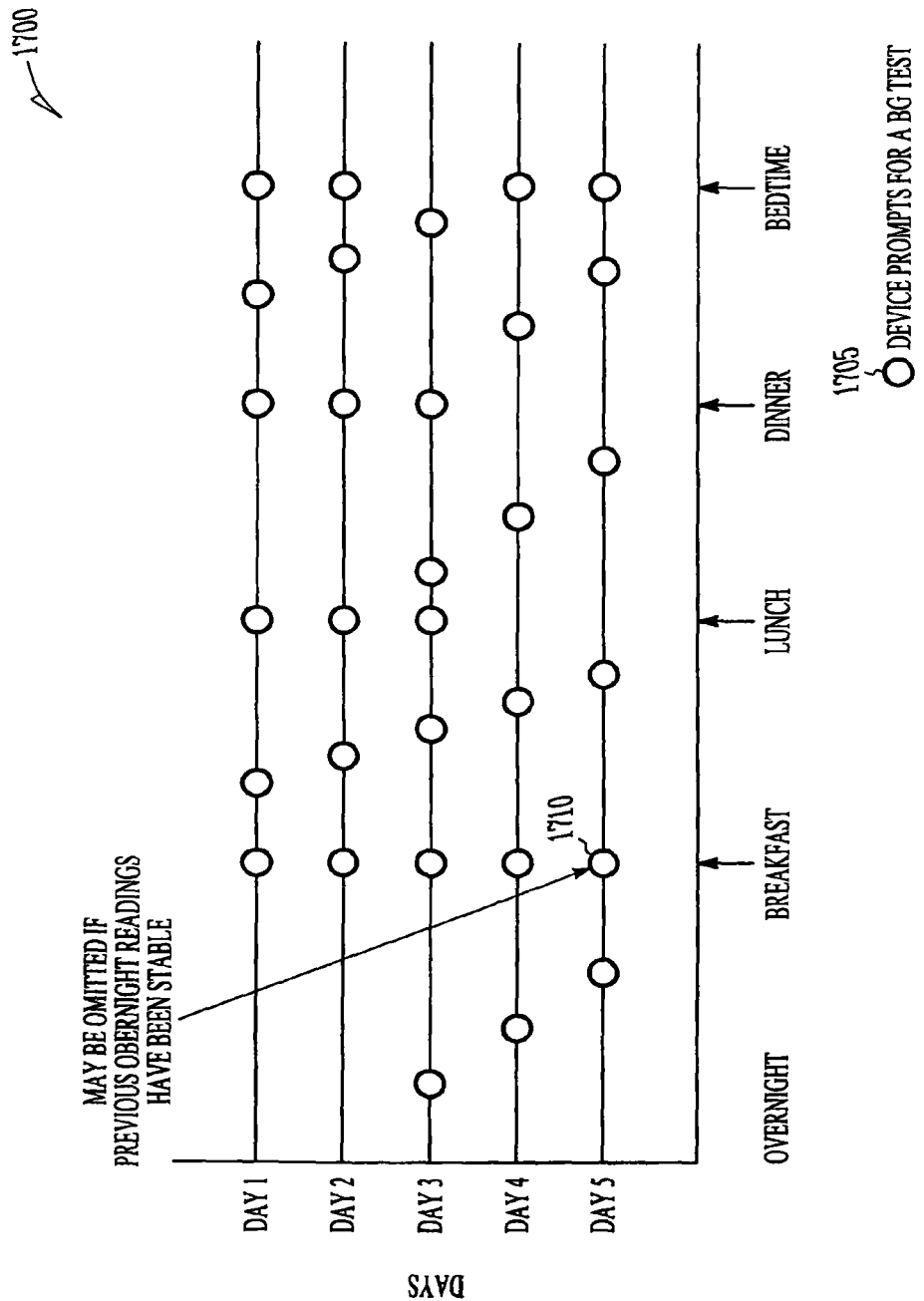
FIG. 17 is a graphical representation of an example of a schedule of blood glucose testing times.

FIG. 17 is a graphical representation of an example of a schedule 1700 or plan of blood glucose testing times. A circle 1705 in the schedule indicates a device 1600 prompt for user to initiate a blood glucose test. The schedule 1700 may be created by the controller 1605 and stored in memory 1640, or an initial schedule 1700 may be programmed into the memory 1640 (e.g., by a care provider) and the controller 1605 adjusts the blood glucose testing times in the schedule 1700 according to the measure of blood glucose variability and/or indicated patient preferences. The schedule 1700 shown illustrates six test times per day over a period of five days, and the prompts are shown in relation to meal times and sleep times of the patient. Throughout the five days, the six testing times are staggered on different days to obtain blood glucose data at various times. The number of days and number of tests per day may be indicated by patient preference in the memory 1640. For the example shown, the controller 1605 may have created the schedule 1700 due to a patient indication of no more than five days of testing per week, no more than six tests per day, and no more than three overnight tests per week. The controller 1605 schedules the testing times based on the preferences and on the historical variation in blood glucose of the patient.

As additional blood glucose data is collected. The controller 1605 may make further adjustments to the schedule 1700. Based on the blood glucose variability, the controller 1605 may change the testing times, add testing times (unless disallowed by preferences), or subtract testing times (as indicated 1710 on day 5). The blood glucose testing plan helps the patient to have a more comprehensive picture of their daily blood glucose by changing the times that the blood glucose tests are requested. According to some embodiments, the device 1600 is a blood glucose monitor. The device 1600 prompts the user to initiate a blood glucose test, such as via the display 1630 for example.

Figure 18:
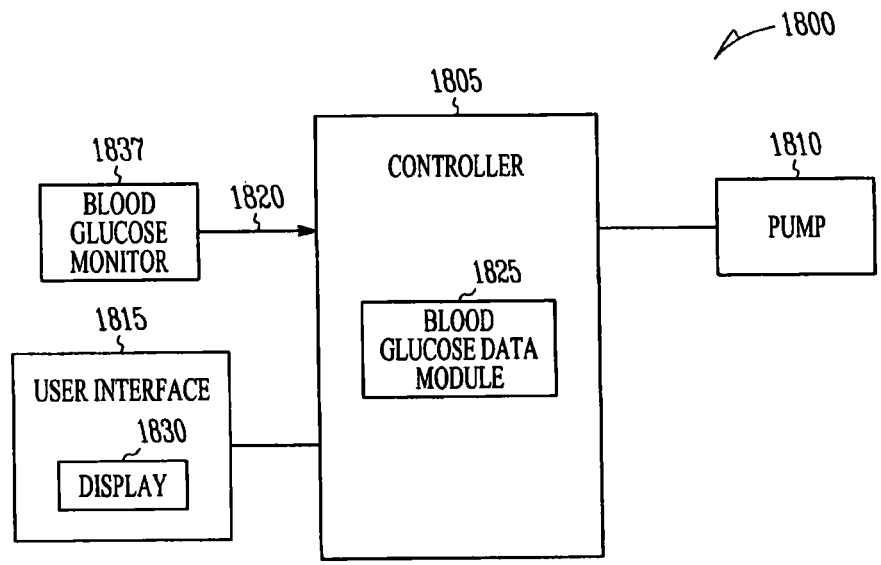
FIG. 18 is a block diagram of portions of another embodiment of a device to determine blood glucose testing times for an insulin pump user.

FIG. 18 is a block diagram of portions of another embodiment of a device 1800 to automatically determine blood glucose testing times for an insulin pump user. The device 1800 includes a controller 1805, a user interface 1815, and an input 1820. The device 1800 also includes a pump 1810 to deliver insulin communicatively coupled to the controller 1805. The input 1820 receives blood glucose data of the insulin pump user into the device 1800. The controller 1805 includes a blood glucose data module 1825 to calculate a measure of the user's blood glucose variability from the blood glucose data.

In some embodiments, the controller 1805 adjusts the blood glucose testing time in response to the measure of blood glucose variability and according to times of insulin delivery. For example, the controller 1805 may schedule a blood glucose testing time to occur a timed duration after the insulin pump user initiates a meal bolus. This may be useful to monitor whether the meal bolus properly controls the user's blood glucose after meal time. In another example, the controller 1805 may schedule a blood glucose testing time to occur a timed duration after a change to a basal insulin rate pattern. This may be useful to monitor the effect of an increase or decrease in basal rate on the user's blood glucose.

In some embodiments, the user interface 1815 includes a display 1830. To obtain blood glucose data the controller 1805 prompts the insulin pump user, via the display 1830, to test blood glucose using a separate device. The controller 1805 adjusts the blood glucose testing times by prompting the user to initiate a blood glucose measurement at a different time. In some embodiments, the user interface 1815 includes one or more keys or buttons, and the user interface 1815 and the input 1820 are configured to receive the blood glucose data by manual entry of the data by the user.

In some embodiments, the device 1800 includes a communication port 1835 communicatively coupled to the input 1820 as shown in FIG. 16. The communication port 1635 may be a wireless port (e.g., an IR or RF port) or a wired port (e.g., a serial port). The controller 1805, 1605 receives the blood glucose data via the communication port 1635 from a separate device (e.g., a blood glucose monitor). The controller 1805, 1605 adjusts the blood glucose testing times by communicating a new testing time via the communication to the separate device, or by providing a prompt for the user to initiate a blood glucose test using the separate device.

In some embodiments, the device 1800 includes a blood glucose monitor 1837 communicatively coupled to the input 1820. The device 1800 receives blood glucose data, via the input 1820, from the blood glucose monitor 1837. In some embodiments, controller 1805 adjusts the blood glucose testing times by generating a prompt to the user to initiate a blood glucose measurement using the blood glucose monitor.

Figure 19:
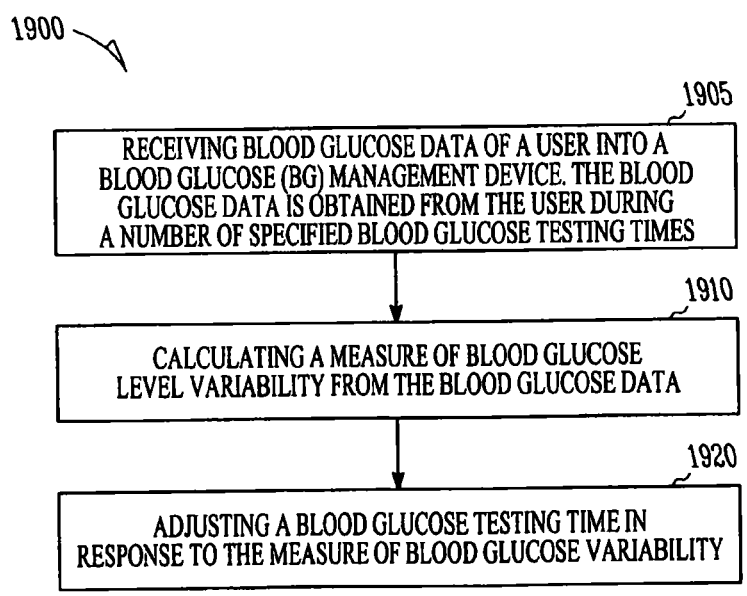
FIG. 19 is a flow diagram of portions of method to determine blood glucose testing times for an insulin pump user.

FIG. 19 is a flow diagram of portions of method 1900 to automatically determine blood glucose testing times for an insulin pump user. At block 1905, blood glucose data of a user of an insulin pump is received into a blood glucose (BG) management device. In some embodiments, the BG management device includes an insulin pump. In some embodiments, the BG management device includes a blood glucose monitor. The blood glucose data is obtained from the user during a number of specified blood glucose testing times.

At block 1910, the BG management device calculates a measure of blood glucose level variability from the blood glucose data. Examples of the variability measurement include a standard deviation of the blood glucose data, an average deviation of the blood glucose data, a variance of the blood glucose data, a range of the blood glucose data, or combinations of the variability measurements.

At block 1915, the BG management device adjusts a blood glucose testing time in response to the measure of blood glucose variability. In some embodiments, the BG management device adjusts a testing time by generating a prompt to initiate testing at an adjusted time. In some embodiments, the BG management device adjusts a testing time by communicating a prompt to initiate a test or measurement to a blood glucose monitor included in the BG management device or included in separate device.

If the blood glucose testing times determined by the BG management device become statistically significant over time, the BG management device helps a patient obtain a better view of their overall blood glucose control.

The above detailed description includes references to the accompanying drawings, which form a part of the detailed description. The drawings show, by way of illustration, specific embodiments in which the invention can be practiced. These embodiments are also referred to herein as "examples." All publications, patents, and patent documents referred to in this document are incorporated by reference herein in their entirety, as though individually incorporated by reference. In the event of inconsistent usages between this document and those documents so incorporated by reference, the usage in the incorporated reference(s) should be considered supplementary to that of this document; for irreconcilable inconsistencies, the usage in this document controls.

In this document, the terms "a" or "an" are used, as is common in patent documents, to include one or more than one. In this document, the term "or" is used to refer to a nonexclusive or, such that "A or B" includes "A but not B," "B but not A," and "A and B," unless otherwise indicated.

It is to be understood that the above description is intended to be illustrative, and not restrictive. For example, the above-described embodiments (and/or aspects thereof) may be used in combination with each other. Many other embodiments will be apparent to those of skill in the art upon reviewing the above description. The scope of the invention should, therefore, be determined with reference to the appended claims, along with the full scope of equivalents to which such claims are entitled. In the appended claims, the terms "including" and "in which" are used as the plain-English equivalents of the respective terms "comprising" and "wherein." Also, in the following claims, the terms "including" and "comprising" are open-ended, that is, a system, device, article, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

The Abstract of the Disclosure is provided to comply with 37 C.F.R. §1.72(b), requiring an abstract that will allow the reader to quickly ascertain the nature of the technical disclosure. It is submitted with the understanding that it will not be used to interpret or limit the scope or meaning of the claims. In addition, in the foregoing Detailed Description, it can be seen that various features are grouped together in a single embodiment for the purpose of streamlining the disclosure. This method of disclosure is not to be interpreted as reflecting an intention that the claimed embodiments require more features than are expressly recited in each claim. Rather, as the following claims reflect, inventive subject matter lies in less than all features of a single disclosed embodiment. Thus the following claims are hereby incorporated into the Detailed Description, with each claim standing on its own.

The invention claimed is:

1. An apparatus comprising:
an input configured to receive blood glucose data, wherein the blood glucose data is obtained during a number of specified blood glucose testing times;
to user interface; and
a controller commicatively coupled to the input, and the user interface, wherein the controller includes:
blood glucose data module configured to calculate statistical measure of blood glucose variability of the user from the blood glucose data, and wherein the controller is configured to automatically adjust a blood glucose testing time from a previously stored testing time in response to the measure of blood glucose variability.

2. The apparatus of claim 1, wherein the controller includes:
a comparison module configured to compare the calculated measure of blood glucose variability to a threshold blood glucose variability value, and wherein the controller is configured to increase the number of blood glucose testing times if the measure of blood glucose variability exceeds a blood glucose variability target value by more than a first threshold blood glucose variability value, and decrease the number of blood glucose testing times if the measure of blood glucose variability is less than the blood glucose variability target value by more than a second threshold blood glucose variability value.

3. The apparatus of claim 1, including a memory communicatively coupled to the controller to store an indication of a user preference for a blood glucose testing time, and wherein the controller is configured to adjust the blood glucose testing time according to the indication.

4. The apparatus of claim 3, wherein the controller is configured to schedule a plurality of blood glucose testing times according to the indication.

5. The apparatus of claim 1, including a blood glucose monitor communicatively coupled to the input and configured to test blood glucose in response to a prompt received from the controller.

6. The apparatus of claim 1, including a communication port coupled to the input and configured to receive blood glucose data from a device separate from the blood glucose management device, and wherein the controller is configured to communicate an adjusted blood glucose testing time to the separate device.

7. The apparatus of claim 1, wherein the user interface includes a display, wherein the controller is configured to prompt a user, via the display, to test blood glucose at an adjusted time using a separate device.

8. The apparatus of claim 7, wherein the user interface is configured to receive manual entry of the blood glucose data from the user.

9. The apparatus of claim 1, including:
a pump communicatively coupled to the controller and configured to deliver insulin, and wherein the controller is configured to adjust the blood glucose testing time in response to the measure of blood glucose variability and according to times of insulin delivery.

* * * * *

UNITED STATES PATENT AND TRADEMARK OFFICE
CERTIFICATE OF CORRECTION

| | | |
|---|---|---|
| PATENT NO. | : 8,718,949 B2 | Page 1 of 2 |
| APPLICATION NO. | : 13/481302 | |
| DATED | : May 6, 2014 | |
| INVENTOR(S) | : Blomquist et al. | |

It is certified that error appears in the above-identified patent and that said Letters Patent is hereby corrected as shown below:

In the specification

Column 2, Line 23:
After "intended" insert -- to --.

Column 3, Lines 29-30:
Delete the second occurrence of "the amount".

Column 7, Line 53:
After "calculates that" insert -- the --.

Column 8, Line 7:
Before "an" delete "and".

Column 8, Line 66:
After "alert may" insert -- be --.

Column 12, Lines 49 and 59:
After "generates" insert -- a --.

Column 13, Line 57:
After "meal" delete "of" and insert -- or --.

Column 17, Line 4:
Delete "return" and insert -- returns --.

Column 18, Line 59:
After "prompt for" insert -- the --.

Signed and Sealed this
Twenty-fourth Day of May, 2016

Michelle K. Lee
*Director of the United States Patent and Trademark Office*

Column 19, Line 13:
Delete "collected. The" and insert -- collected, the --.

Column 20, Line 32:
After "included in" insert -- a --.

In the claims

Column 21, Line 27:
Delete "to user" and insert -- a user --.

Column 21, Line 30:
Before "blood glucose" insert -- a --; after "calculate" insert -- a --.

Column 22, Lines 23-24:
After "from a" delete "device" and after "separate" delete "from the blood glucose management".

Column 22, Line 28:
After "display," insert -- and --.